United States Patent
Clausen et al.

(10) Patent No.: US 12,365,674 B2
(45) Date of Patent: Jul. 22, 2025

(54) INHIBITORS OF HISTONE DEACETYLASE USEFUL FOR THE TREATMENT OR PREVENTION OF HIV INFECTION

(71) Applicant: Merck Sharp & Dohme LLC, Rahway, NJ (US)

(72) Inventors: Dane James Clausen, Rahway, NJ (US); Joseph A. Kozlowski, Princeton, NJ (US); Jian Liu, Edison, NJ (US); Scott E. Wolkenberg, Wyndmoor, PA (US); Wengsheng Yu, Edison, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 982 days.

(21) Appl. No.: 17/422,642

(22) PCT Filed: Jan. 10, 2020

(86) PCT No.: PCT/US2020/013080
§ 371 (c)(1),
(2) Date: Jul. 13, 2021

(87) PCT Pub. No.: WO2020/150091
PCT Pub. Date: Jul. 23, 2020

(65) Prior Publication Data
US 2022/0089585 A1   Mar. 24, 2022

Related U.S. Application Data

(60) Provisional application No. 62/792,455, filed on Jan. 15, 2019.

(51) Int. Cl.
| | | |
|---|---|---|
| C07D 413/14 | (2006.01) |
| A61K 31/422 | (2006.01) |
| A61K 31/4709 | (2006.01) |
| A61K 45/06 | (2006.01) |
| A61P 31/18 | (2006.01) |
| C07D 413/12 | (2006.01) |
| C07D 417/14 | (2006.01) |

(52) U.S. Cl.
CPC ......... *C07D 413/14* (2013.01); *A61K 31/422* (2013.01); *A61K 31/4709* (2013.01); *A61K 45/06* (2013.01); *A61P 31/18* (2018.01); *C07D 413/12* (2013.01); *C07D 417/14* (2013.01)

(58) Field of Classification Search
CPC .. C07D 413/14; C07D 413/12; C07D 417/14; A61K 31/422; A61K 31/4709; A61K 45/06; A61P 31/18
See application file for complete search history.

(56) References Cited

U.S. PATENT DOCUMENTS

| | | | |
|---|---|---|---|
| 2005/0282890 A1* | 12/2005 | Lan-Hargest | A61P 35/00 514/475 |
| 2009/0048228 A1 | 2/2009 | Attenni et al. | |
| 2015/0299163 A1 | 10/2015 | Altamura et al. | |
| 2016/0279069 A1* | 9/2016 | Jayant | A61K 31/683 |

FOREIGN PATENT DOCUMENTS

| | | |
|---|---|---|
| WO | 2007052073 A2 | 5/2007 |
| WO | 2007072080 A2 | 6/2007 |
| WO | 2014023754 A1 | 2/2014 |

OTHER PUBLICATIONS

Kinzel O, Llauger-Bufi L, Pescatore G, Rowley M, Schultz-Fademrecht C, Monteagudo E, Fonsi M, Gonzalez Paz O, Fiore F, Steinkühler C, Jones P. J Med Chem. Jun. 11, 2009;52(11):3453-6. (Year: 2009).*
Kinzel (Kinzel et al., J. Med. Chem. 2009, 52, 3453-3456, made of record on the IDS (Year: 2009).*
Rautio J, Meanwell NA, Di L, Hageman MJ. The expanding role of prodrugs in contemporary drug design and development. Nat Rev Drug Discov. Aug. 2018;17(8):559-58 (Year: 2018).*
Kinzel et al., J. Med. Chem. 2009, 52, 3453-3456, made of record on the IDS (Year: 2009).*
Kinzel, Olaf et al., Discovery of a Potent Class I Selective Ketone Histone Deacetylase Inhibitor with Antitumor Activity in Vivo and Optimized Pharmacokinetic Properties, J. Med. Chem., 2009, 3453-3456, 52.
Bresciani, Alberto et al., Improved Selective Class I HDAC and Novel Selective HDAC3 Inhibitors: Beyond Hydroxamic Acids and Benzamides, ACS Med. Chem. Lett., 2019, 481-486, 10(4).

* cited by examiner

*Primary Examiner* — Clinton A Brooks
*Assistant Examiner* — Izabela Schmidt
(74) *Attorney, Agent, or Firm* — Eric Greenwald; John C. Todaro

(57) ABSTRACT

The present invention relates to Compounds of Formula I and pharmaceutically acceptable salts or prodrug thereof, wherein $R^1$, $R^2$, $R^3$, $R^4$, X and A are as defined herein. The present invention also relates to compositions comprising at least one compound of Formula I, and methods of using the compounds of Formula I for treating or preventing HIV infection in a subject.

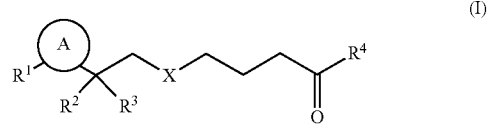

(I)

9 Claims, No Drawings

INHIBITORS OF HISTONE DEACETYLASE USEFUL FOR THE TREATMENT OR PREVENTION OF HIV INFECTION

CROSS REFERENCE TO RELATED APPLICATIONS

This application is a U.S. National Phase application under 35 U.S.C. § 371 of PCT Application No. PCT/US2020/013080 filed Jan. 10, 2020, which claims priority from U.S. Ser. No. 62/792,455 filed Jan. 15, 2019.

FIELD OF THE INVENTION

The present invention relates to inhibitors of histone deacetylase, compositions comprising at least one inhibitor of histone deacetylase, and methods of using the inhibitors of histone deacetylase for treating or preventing HIV infection in a subject.

BACKGROUND OF THE INVENTION

DNA in the nucleus of the cell exists as a hierarchy of compacted chromatin structures. The basic repeating unit in chromatin is the nucleosome, which consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function, and ultimately, gene expression. The covalent modification of histones, such as acetylation, occurs by enzymatically mediated process.

Regulation of gene expression through the inhibition of the nuclear enzyme histone deacetylase (HDAC) is one of the several possible regulatory mechanisms whereby chromatin actively can be affected. The dynamic homeostasis of the nuclear acetylation of histone can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. While histone acetylation can activate DNA transcription, enhancing gene expression, histone deacetylase can reverse the process and can serve to repress gene expression. Inhibition of the histone deacetylase (HDAC inhibition) can also increase the activation of DNA transcription. See, for example, Grunstein, Nature, 389, 349-352 (1997); Pazin et al., Cell 89, 325-328 (1997); Wade et al., Trends Biochem Sci. 22, 128-132 (1997); and Wolffe, Science 272, 371-372 (1996).

With the introduction of combination antiretroviral therapy (ART), HIV became a controllable chronic disease. The combination of ART (cART) targets specific stages of the viral life cycle, and is effective at combatting active viral load down to undetectable levels. However, HIV persists within the body of infected individuals undergoing therapy, and cessation of ART leads to a viral rebound within 3-4 weeks. The HIV can persist in resting memory and naïve CD4+ T cells and other long-lived cells, such as infected astrocytes and cells of macrophage lineage. HIV can persist in these resting cells by establishing a latent or "silent" infection. In these cells, virus is integrated into the host genome, but viral production does not occur as a result of inhibition of both viral transcriptions from proteins. However, these latently infected cells still do contain replication competent virus, and once cART is stopped, rebound in plasma HIV RNA is observed in nearly all patients.

One approach currently being explored to eliminate latently infected CD4+ T cells is to activate viral production from these cells in the presence of cART, when the production of the virus should kill the infected cells. Histone deacetylase inhibitors have shown promise in vitro in activating virus production from latent infected cells, and therefore this class of drugs is being studied as part of a strategy aimed at a cure of HIV.

Eleven members of the HDAC family has been identified in humans, which share a conserved catalytic domain and are grouped into two classes: class I (1,2,3,8), homologous to yeast Rpd3; and class IIa (4,5,7,9) and IIb (6, 10), homologous to yeast Hdal. HDAC 11 shares homology with both classes, but is at the same time distinct from all the other ten subtypes. The first generation of HDAC inhibitors (HDACi) are promising therapeutic agents against cancer and other diseases, and showed in vitro activation of virus production from latent infected cells. However, due to their poor selectivity, those that entered clinical trials, all show similar adverse effects. The poorly selective HDACi's are not suitable for healthy HIV patents on cART, thus the interest is high for the discovery and development of novel and subtype selective HDAC inhibitors.

SUMMARY OF THE INVENTION

In one aspect, the present invention provides Compounds of Formula I:

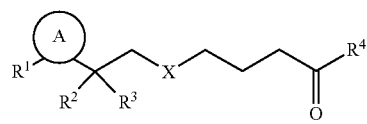

or a pharmaceutically acceptable salt thereof,
wherein X is O, S or $SO_2$;

is a five-membered heteroaryl ring which is optionally substituted with halo, cyano or $C_{1-3}$ alkyl;

$R^1$ is phenyl or heteroaryl, which may be monocyclic or bicyclic, wherein said phenyl and heteroaryl groups are optionally substituted with one to three groups independently selected from the group consisting of halo, oxo, cyano, $R^5$, $R^6$, $OR^5$, $OR^6$ and $SO_2R^5$;

$R^2$ is selected from the group consisting of hydrogen, $NHR^5$, $NH(C=O)R^5$ and $NH(C=O)R^6$;

$R^3$ is hydrogen or $C_{1-6}$ alkyl;

$R^4$ is ethyl, heteroaryl or $(C=O)NHR^5$, wherein said heteroaryl group is optionally substituted with $C_{1-6}$ alkyl;

each $R^5$ is independently hydrogen or $C_{1-6}$ alkyl, which is optionally substituted with $NH_2$, $N(CH_3)_2$, $NH(CH_3)$ or one to three halo;

$R^6$ is
(a) heterocyclyl, which may be monocyclic, bicyclic or tricyclic,
(b) $C_{3-6}$ cycloalkyl,
(c) phenyl, or
(d) heteroaryl, which may be monocyclic, bicyclic or tricyclic,
wherein said heterocyclyl, cycloalkyl, phenyl and heteroaryl groups are optionally substituted with one to two groups independently selected from the group consisting of halo, cyano, oxo, $R^5$, and $OR^5$.

The Compounds of Formula I and pharmaceutically acceptable salts or prodrugs thereof may be useful, for example, for activating HIV latency for potential complete cure of HIV infection alone or in combination with cART and/or other HIV treatments.

Accordingly, the present invention provides methods for treating or preventing HIV infection in a subject, comprising administering to the subject an effective amount of at least one compound of Formula I.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to inhibitors of histone deacetylase, compositions comprising at least one inhibitor of histone deacetylase, and methods of using the inhibitors of histone deacetylase for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of the compound of Formula I and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prophylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofuranyl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^5$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula I or a pharmaceutically acceptable salt of the compound. The transformation may occur by various mechanisms (e.g., by metabolic or chemical processes), such as, for example, through hydrolysis in blood. For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolactone-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula I contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6)$alkanoyloxy)ethyl, 1-methyl-1-(($C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$ alkyl, $(C_3-C_7)$ cycloalkyl, benzyl, a natural α-aminoacyl, —C(OH)C(O)OY¹ wherein Y¹ is H, $(C_1-C_6)$alkyl or benzyl, —C(OY²)Y³ wherein Y² is $(C_1-C_4)$ alkyl and Y³ is $(C_1-C_6)$ alkyl; carboxy $(C_1-C_6)$alkyl; amino$(C_1-C_4)$alkyl or mono-N— or di-N,N—$(C_1-C_6)$alkylaminoalkyl; —C(Y⁴)Y⁵ wherein Y⁴ is H or methyl and Y⁵ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulphonyl (for example, methanesulfonyl); (3) amino acid esters, including those corresponding to both natural and non-natural amino acids (e.g., L-valyl or L-isoleucyl); (4) phosphonate esters and (5) mono-, di- or tri-phosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalene-sulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the compound of Formula I may be atropisomers (e.g., substituted biaryls) and are considered as part of this invention. Enantiomers can also be directly separated using chiral chromatographic techniques.

It is also possible that the compound of Formula I may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

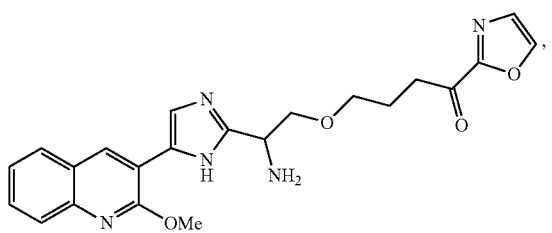 [SMILES: COc1nc2ccccc2cc1-c1cnc(C(N)COCCCC(=O)c2ncco2)[nH]1]

is understood to encompass both stereoisomers at the indicated chiral center, the structures of which are as follows:

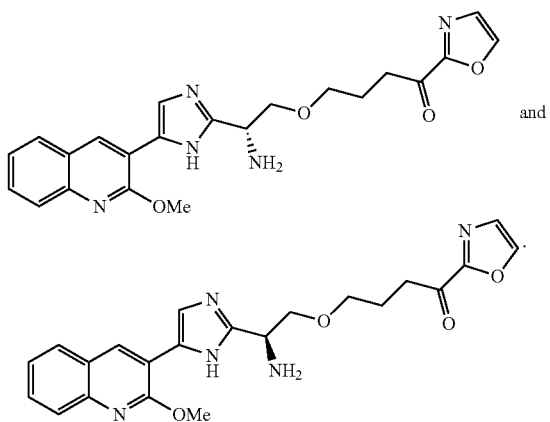

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I has one or more of its hydrogen atoms replaced with deuterium.

The compounds of Formula I may be useful in human and veterinary medicine for treating or preventing HIV infection in a subject. In one embodiment, the compounds of Formula I can be inhibitors of HIV viral replication. In a specific embodiment, the compound of Formula I are inhibitors of HIV-1. Accordingly, the compounds of Formula I may be useful for treating HIV infections and AIDS. In accordance with the invention, the compounds of Formula I can be administered to a subject in need of treatment or prevention of HIV infection.

Accordingly, in one embodiment, the invention provides methods for treating HIV infection in a subject comprising administering to the subject an effective amount of at least one compound of Formula I or a pharmaceutically acceptable salt thereof. In a specific embodiment, the present invention provides methods for treating AIDS in a subject comprising administering to the subject an effective amount of at least one compound of Formula I or a pharmaceutically acceptable salt thereof.

The Compounds of Formula I

The present invention provides Compounds of Formula I:

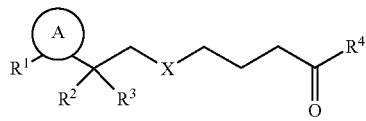

wherein X is O, S or SO$_2$;

is a five-membered heteroaryl ring which is optionally substituted with halo, cyano or C$_{1-3}$ alkyl;

R$^1$ is phenyl or heteroaryl, which may be monocyclic or bicyclic, wherein said phenyl and heteroaryl groups are optionally substituted with one to three groups independently selected from the group consisting of halo, oxo, cyano, R$^5$, R$^6$, OR$^5$, OR$^6$ and SO$_2$R$^5$;

R$^2$ is selected from the group consisting of hydrogen, NHR$^5$, NH(C=O)R$^5$ and NH(C=O)R$^6$;

R$^3$ is hydrogen or C$_{1-6}$ alkyl;

R⁴ is ethyl, heteroaryl or (C=O)NHR⁵, wherein said heteroaryl group is optionally substituted with $C_{1-6}$ alkyl;

each R⁵ is independently hydrogen or $C_{1-6}$ alkyl, which is optionally substituted with $NH_2$, $N(CH_3)_2$, $NH(CH_3)$ or one to three halo;

R⁶ is
(a) heterocyclyl, which may be monocyclic, bicyclic or tricyclic,
(b) $C_{3-6}$ cycloalkyl,
(c) phenyl, or
(d) heteroaryl, which may be monocyclic, bicyclic or tricyclic,
wherein said heterocyclyl, cycloalkyl, phenyl and heteroaryl groups are optionally substituted with one to two groups independently selected from the group consisting of halo, cyano, oxo, R⁵, and OR⁵;

or a pharmaceutically acceptable salt thereof.

In an embodiment of the invention, (A)

is imidazolyl, which is optionally substituted with halo. In a class of the embodiment, (A)

is imidazolyl. In another embodiment of the invention, (A)

is imidazolyl substituted with chloro.

In an embodiment of the invention, X is O. In another embodiment of the invention, X is S. In another embodiment of the invention, X is $SO_2$.

In an embodiment of the invention, R¹ is phenyl or quinolinyl, wherein said groups are optionally substituted with one to three groups optionally selected from the group consisting of halo, R⁵ and OR⁵. In a class of the invention, R¹ is phenyl, which is optionally substituted with halo. In another class of the invention, R¹ is quinolinyl, which optionally substituted with one or two groups optionally selected from the group consisting of R⁵ and OR⁵. In a subclass of the invention, R¹ is quinolinyl, which optionally substituted with one or two groups optionally selected from the group consisting of $CH_3$ and $OCH_3$.

In an embodiment of the invention, R² is NH(C=O)R⁶, and R⁶ is selected from the group consisting of azabicyclooctanyl, azetidinyl, azaspirooctanyl, and thiazolyl, wherein said azetidinyl and azaspirooctanyl groups are optionally substituted with methyl or ethyl. In another embodiment of the invention, R² is $NH_2$.

In an embodiment of the invention, R³ is hydrogen.

In an embodiment of the invention, R⁴ is ethyl. In another embodiment of the invention, R⁴ is (C=O)$NHCH_3$. In another embodiment of the invention, R⁴ is oxazolyl. In another embodiment of the invention, R⁴ is oxazolyl substituted with $CH_3$.

In another embodiment, the Compounds of Formula I are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula I, and a pharmaceutically acceptable carrier.

(b) The pharmaceutical composition of (a), further comprising a second therapeutic agent selected from the group consisting of HIV antiviral agents, immunomodulators, anti-infective agents, vaccines, and antibodies.

(c) The pharmaceutical composition of (b), wherein the HIV antiviral agent is an antiviral selected from the group consisting of HIV protease inhibitors, HIV integrase inhibitors and HIV NNRTI inhibitors.

(d) A pharmaceutical combination that is (i) a Compound of Formula I and (ii) a second therapeutic agent selected from the group consisting of HIV antiviral agents, immunomodulators, and anti-infective agents, vaccines, and antibodies; wherein the Compound of Formula I and the second therapeutic agent are each employed in an amount that renders the combination effective for inhibiting HIV replication, or for treating HIV infection and/or reducing the likelihood or severity of symptoms of HIV infection, and eradicates HIV infection.

(e) The combination of (d), wherein the HIV antiviral agent is an antiviral selected from the group consisting of HIV protease inhibitors, HIV integrase inhibitors and HIV NNRTI inhibitors.

(f) A method of inhibiting HIV replication in a subject in need thereof which comprises administering to the subject an effective amount of a Compound of Formula I.

(g) A method of treating HIV infection and/or reducing the likelihood or severity of symptoms of HIV infection in a subject in need thereof which comprises administering to the subject an effective amount of a Compound of Formula I.

(h) The method of (g), wherein the Compound of Formula I is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula I, and a pharmaceutically acceptable carrier.

(m) The pharmaceutical composition of (l), further comprising a second therapeutic agent selected from the group consisting of HIV antiviral agents, immunomodulators, anti-infective agents, vaccines and antibodies.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula I and (ii) a second therapeutic agent selected from the group consisting of HIV antiviral agents, immunomodulators, and anti-infective agents; wherein the pharmaceutically acceptable salt of the Compound of Formula I and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula I.

(r) A method of treating HIV infection and/or reducing the likelihood or severity of symptoms of HIV infection in a subject in need thereof which comprises administering to the subject an effective amount of a pharmaceutically acceptable salt of a Compound of Formula I.

(s) The method of (r), wherein the pharmaceutically acceptable salt of the Compound of Formula I is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula I or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula I and (ii) or a pharmaceutically acceptable salt thereof, a second therapeutic agent selected from the group consisting of HIV antiviral agents, immunomodulators, and anti-infective agents; wherein the Compound of Formula I and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula I or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula I or a pharmaceutically acceptable salt thereof.

(dd) The method of (cc), wherein the Compound of Formula I or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w), (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use I in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula I include compounds 1-21 as set forth in the Examples below, and pharmaceutically acceptable salts thereof Methods for Making the Compounds of Formula I The Compounds of Formula I may be prepared from known or readily prepared starting materials, following methods known to one skilled in the art of organic synthesis. Methods useful for making the Compounds of Formula I are set forth in the Examples below and generalized in the Schemes below. Alternative synthetic pathways and analogous structures will be apparent to those skilled in the art of organic synthesis.

General List of Abbreviations

Abbreviations and acronyms employed herein include the following:

| | |
|---|---|
| Ac | Acetyl |
| Aq | Aqueous |
| ACN | Acetonitrile |
| AIBN | Azobisisobutyronitrile |
| AUC | Area under the curve |
| BAST | Bis(2-methoxyethyl)aminosulfur trifluoride |
| BOC | tert-butyloxycarbonyl |
| BPD | Bis(pinacolato)diboron |
| Bu | Butyl |
| Bz | Benzoyl |
| CDI | Carbonyldiimidazole |
| DBDMH | 1,3-Dibromo-5,5-dimethylhydantoin |
| DBU | 1,8-Diazabicyclo[5.4.0]undec-7-ene |
| DCM | Dichloromethane |
| DCE | 1,2-Dichloroethane |
| DHP | 3,4-dihydro-2H-pyran |
| DIBAL-H | Diisobutylaluminium hydride |
| DIEA, DIPEA or Hünig's base | N,N-diisopropylethylamine |
| DMAP | 4-dimethylaminopyridine |
| DME | dimethyoxyethane |
| DMF | dimethylformamide |
| DMP | Dess-Martin periodinane |
| Dppf | 1,1'-Bis(diphenylphosphino)ferrocene |
| DMSO | dimethyl sulfoxide |
| DTBPF | 1,1'-bis(di-tert-butylphosphino)ferrocene |
| EA | Ethyl Acetate |
| EDC | 1-Ethyl-3-(3-dimethylaminopropyl)carbodiimide hydrochloride |
| EDCI | N-ethyl-N'-(3-dimethylaminopropyl)carbodiimide hydrochloride |
| Et | Ethyl |
| EtOH | Ethanol |
| EtOAc | ethyl acetate |
| G | Grams |
| GI | Gastrointenstinal |
| H | Hour |
| HATU | 1-[Bis(dimethylamino)methylene]-1H-1,2,3-triazolo[4,5-b]pyridinium 3-oxide hexafluorophosphate |
| HIV | human immunodeficiency virus |
| HOBT, HOBt | 1-Hydroxybenzotriazole hydrate |
| HPBCD | hydroxypropyl β-cyclodextrin |
| HPLC | high-performance liquid chromatography |
| mCPBA, CPBA | meta-Chloroperoxybenzoic |
| Hz | Hertz |
| IPA | Isopropanol |
| IV | Intravenous |
| iPr | Isopropyl |
| Ir[dF(CF$_3$)ppy]$_2$(dtbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| L | Liter |
| LC | liquid chromatography |
| LC/MS | liquid chromatography mass spectrometry |
| LED | light-emitting diode |
| LiHMDS | lithium bis(trimethysilyl)amide |
| Me | Methyl |
| MeOH | Methanol |
| Mg | Milligrams |
| MHz | Megahertz |
| Min | Minute |
| μL | Microliters |
| mL | Milliliters |
| Mmol | Millimoles |
| MOM-Cl | chloromethyl methyl ether |
| MPLC | medium pressure liquid chromatography |
| MS | mass spectrometry |
| NBS | N-Bromosuccinimide |
| NCS | N-Chlorosuccinimide |
| NHS | normal human serum |
| NIS | N-Iodosuccinimide |
| NMO | 4-methylmorpholine N-oxide |
| NMR | nuclear magnetic resonance spectroscopy |
| PBMC | peripheral blood mononuclear cell |
| Pd$_2$(dba)$_3$ | Tris(dibenzylideneacetone)dipalladium(0) |
| Ph | Phenyl |
| P.O. | Oral |
| PPTS | Pyridinium p-toluenesulfonate |
| PTSA | para-toluenesulfonic acid |
| Pr | Propyl |
| Rpm | revolutions per minute |
| RT or rt | room temperature (ambient, about 25° C.) |
| sat or sat'd | Saturated |
| SEMCl | 2-Chloromethoxyethyl)trimethylsilane |
| SFC | supercritical fluid chromatography |
| T3P, T$_3$P | 1-Propanephosphonic anhydride solution |
| TBAF | Tetra-n-butylammonium fluoride |
| TBDPSCl | tert-Butyldiphenylchlorosilane |
| TBSCl | tert-Butyldimethylsilyl chloride |
| tBu | tert-butyl |
| TEA | triethylamine (Et$_3$N) |
| TEMED | Tetramethylethylenediamine |
| TFA | trifluoroacetic acid |
| TFV | Tenofovir |
| TFV-MP | Tenofovir monophosphoate |
| TFV-DP | Tenofovir diphosphate |
| THF | Tetrahydrofuran |
| TMS | Tetramethylsilane |
| TosMIC | Toluenesulfonylmethyl isocyanide |
| TPAP | Tetrapropylammonium perruthenate |
| Ts | Tosyl |
| UPLC | ultrahigh pressure liquid chromatography |
| UV | Ultraviolet |
| UV/VIS | ultraviolet/visible |
| W | Watt |
| XPhos | 2-Dicyclohexylphosphino-2',4',6'-triisopropylbiphenyl |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60E-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC® BEH C18 1.0×50 mm, 1.7 μm. The flow rate was 0.3 mL/min, and the injection volume was 0.5 µL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 mL/min for the Waters SUNFIRE™ column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was most commonly performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% EtOH/CO$_2$), or isopropanol in carbon dioxide (% IPA/CO$_2$) as isocratic solvent systems. Chiral preparative chromatography was conducted on one of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several catalysts are used in the following procedures. "UMICORE M71 SIPR" is also known as Umicore Hoveyda Grubbs Catalyst M71 SIPr" and [1,3-Bis(2,6-diisopropylphenyl)-2-imidazolidinylidene]dichloro[(2-isopropoxy) (5-trifluoroacetamido)benzylidene]ruthenium(II). It is available from Umicore Precious Metals Chemistry USA, LLC, 1305 Main Parkway Catoosa, OK 74015. "Zhan's catalyst" is available from Sigma Aldrich. "XPhos Palladium G3" is also known as (2-dicyclohexylphosphino-2',4', 6'-triisopropyl-1,1'-biphenyl)[2-(2'-amino-1,1'-biphenyl)] palladium(II) methanesulfonate, and is available from Sigma Aldrich. "Zhan Catalyst-1B" is also known as (Dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II)) and is available from Sigma Aldrich.

Several methods for preparing the compounds of this invention are also described in the Examples. Starting materials and intermediates were purchased commercially from common catalog sources or were made using known procedures, or as otherwise illustrated.

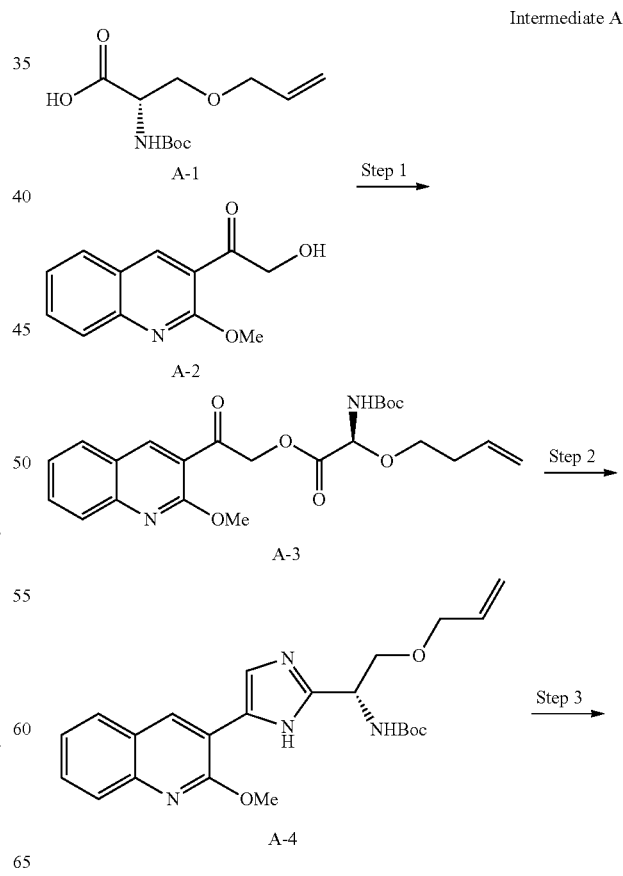

Intermediate A

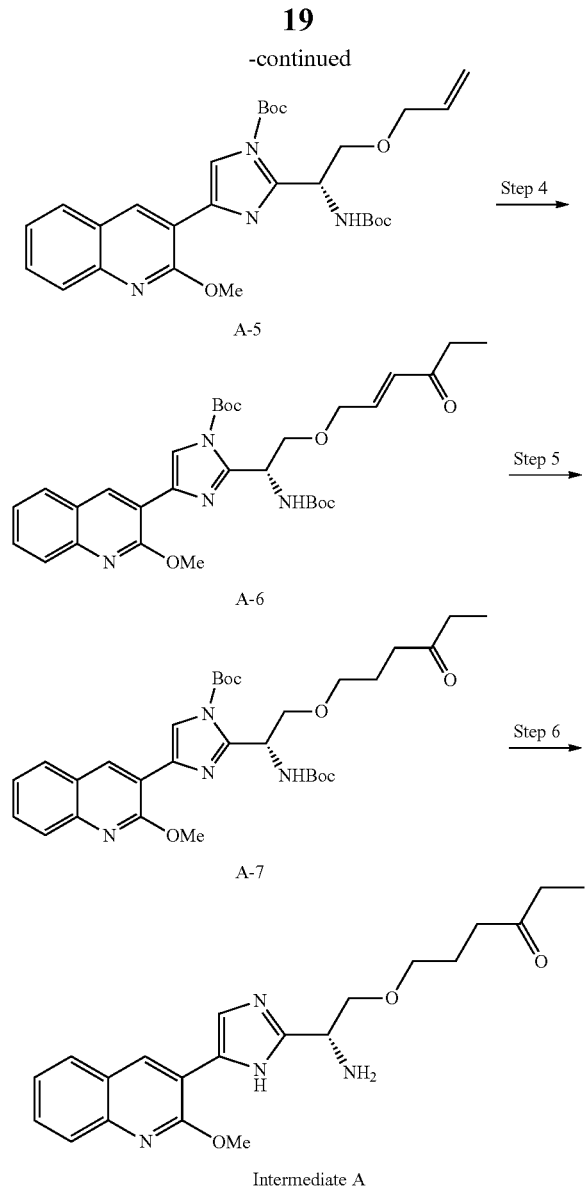

Intermediate A

Step 1: 2-(2-methoxyquinolin-3-yl)-2-oxoethyl O-allyl-N-(tert-butoxycarbonyl)-L-serinate (A-3)

To a solution of (S)-3-(allyloxy)-2-((tert-butoxycarbonyl) amino)propanoic acid (A-1) (3.39 g, 13.81 mmol) in DCM (18.41 ml) at ambient temperature was added 2-hydroxy-1-(2-methoxyquinolin-3-yl)ethanone (A-2) (2.0 g, 9.21 mmol), EDC (2.118 g, 11.05 mmol), HOBT (1.692 g, 11.05 mmol), and DIPEA (3.22 ml, 18.41 mmol). The mixture stirred for 4 hours before quenching with $H_2O$ (40 mL), extracting with DCM (40 mL×3), drying over $Na_2SO_4$, and concentrating. The residue was purified by column chromatography on silica (5-50% 1:3 EtOH:EtOAc/hexanes) to afford the title compound. MS: 445.2 (M+1).

Step 2: tert-butyl (R)-(2-(allyloxy)-1-(5-(2-methoxyquinolin-3-yl)-1H-imidazol-2-yl)ethyl)carbamate (A-4)

To a solution of (S)-2-(2-methoxyquinolin-3-yl)-2-oxoethyl 3-(allyloxy)-2-((tert-butoxycarbonyl)amino)propanoate (A-3) (3.00 g, 6.75 mmol) in Toluene (22.50 ml) at ambient temperature was added ammonium acetate (2.60 g, 33.7 mmol). The reaction mixture was heated to 95° C. overnight. The reaction was cooled and neutralized with a saturated solution of $NaHCO_3$(50 mL). The mixture was extracted with EtOAc (50 mL×3), dried over $Na_2SO_4$, and concentrated. The residue was purified by column chromatography on silica (5-80% 1:3 EtOH:EtOAc/hexanes) to afford the title compound. MS: 425.3 (M+1).

Step 3: tert-butyl (R)-2-(2-(allyloxy)-1-((tert-butoxycarbonyl)amino)ethyl)-4-(2-methoxyquinolin-3-yl)-1H-imidazole-1-carboxylate (A-5)

To a solution of (R)-tert-butyl(2-(allyloxy)-1-(5-(2-methoxyquinolin-3-yl)-1H-imidazol-2-yl)ethyl)carbamate (A-4) (1.80 g, 4.24 mmol) in DCM (8.48 ml) at ambient temperature was added $BOC_2O$ (1.083 ml, 4.66 mmol), DMAP (0.026 g, 0.212 mmol), and $Et_3N$ (0.650 ml, 4.66 mmol). The reaction mixture was stirred for 1 hour before concentrating. The residue was purified by column chromatography on silica (2-30% 1:3 EtOH:EtOAc) to afford the title compound. MS: 525.3 (M+1).

Step 4: tert-butyl (R,E)-2-(1-((tert-butoxycarbonyl)amino)-2-((4-oxohex-2-en-1-yl)oxy)ethyl)-4-(2-methoxyquinolin-3-yl)-1H-imidazole-1-carboxylate (A-6)

To a solution of (R)-tert-butyl 2-(2-(allyloxy)-1-((tert-butoxycarbonyl)amino)ethyl)-4-(2-methoxyquinolin-3-yl)-1H-imidazole-1-carboxylate (A-5) (550 mg, 1.048 mmol) in DCM (2.10 ml) at ambient temperature was added pent-1-en-3-one (311 µl, 3.15 mmol) and Zhan Catalyst—1B (38.5 mg, 0.052 mmol). The reaction mixture stirred for 2 hours before the mixture was concentrated. The residue was purified by column chromatography on silica (2-40% 1:3 EtOH:EtOAc/hexanes) to afford the title compound. MS: 581.4 (M+1).

Step 5: tert-butyl (R)-2-(1-((tert-butoxycarbonyl)amino)-2-((4-oxohexyl)oxy)ethyl)-4-(2-methoxyquinolin-3-yl)-1H-imidazole-1-carboxylate (A-7)

To a solution of (R,E)-tert-butyl 2-(1-((tert-butoxycarbonyl)amino)-2-((4-oxohex-2-en-1-yl)oxy)ethyl)-4-(2-methoxyquinolin-3-yl)-1H-imidazole-1-carboxylate (A-6) (600 mg, 1.033 mmol) in MeOH (6.89 ml)/THF (3.44 mL) at ambient temperature was added Pd/C (110 mg, 0.103 mmol). A balloon of hydrogen was added (vacuum purge 3×) and the reaction stirred overnight. The mixture was filtered through a pad of celite and the filtrate was concentrated. The residue was purified by column chromatography on silica (2-40% 1:3 EtOH:EtOAc/hexanes) to afford the title compound. MS: 583.4 (M+1).

Step 6: (R)-6-(2-amino-2-(5-(2-methoxyquinolin-3-yl)-1H-imidazol-2-yl)ethoxy)hexan-3-one (Intermediate A)

To a solution of (R)-tert-butyl 2-(1-((tert-butoxycarbonyl)amino)-2-((4-oxohexyl)oxy)ethyl)-4-(2-methoxyquinolin-3-yl)-1H-imidazole-1-carboxylate (A-7) (600 mg, 1.030 mmol) in DCM (5149 µl) at ambient temperature was added TFA (397 µl, 5.15 mmol). The reaction stirred for 2 hours before concentrating. The residue was purified by mass triggered reverse phase HPLC (MeCN/water with 0.1% TFA modifier) to afford the title compound. MS: 383.2 (M+1).

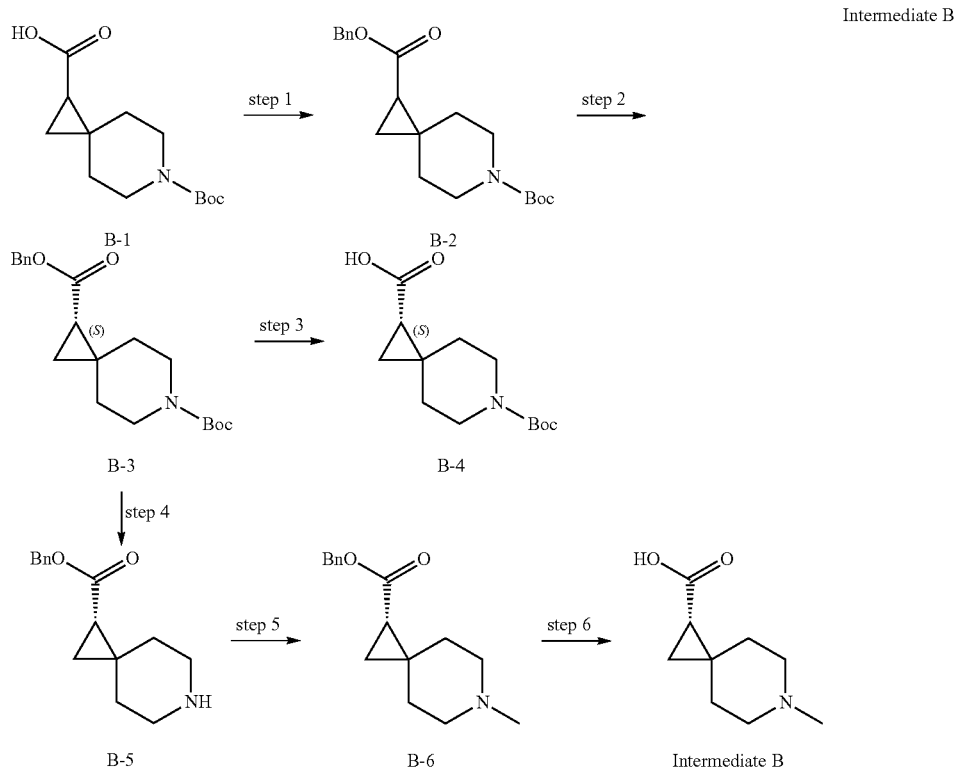

Intermediate B

Step 1: 1-benzyl 6-tert-butyl 6-azaspiro[2.5]octane-1,6-dicarboxylate (B-2)

Two reactions were carried out in parallel.

DBU (235 g, 1.55 mol, 233 mL) was added in one portion to a solution of 6-(tert-butoxycarbonyl)-6-azaspiro[2.5]octane-1-carboxylic acid (B-1, 330 g, 1.29 mol) in $CH_3CN$ (3.3 L) at 20° C. to afford a light yellow suspension. Benzyl bromide (242 g, 1.42 mol, 168 mL) was added to the suspension in one portion at 20° C. The suspension was stirred at 20° C. for 4 h. Two reactions were combined and concentrated. Ethyl acetate (5.5 L) was added to dissolve the residual, and precipitate appeared which was filtered and the filter cake was washed with ethyl acetate (300 mL*3). The organic phase was washed with citric acid (10% w/w, 3 L*2), sat.$NaHCO_3$ aqueous (3 L*2), water (2 L) and brine (2 L) in sequence. The organic phase was dried over $Na_2SO_4$. It was filtered and concentrated to give crude product.

The crude product was dissolved with petroleum ether (7 L) and the solution was put in a dry ice-acetone bath for 12 h and a solid appeared. The solution was poured out and the solid ground with petroleum ether (600 mL) for 1 hour. The suspension was filtered and the filter cake was washed with petroleum ether (30 mL*2) to get filter cake (400 g).

The mother solution was combined and concentrated in vacuole; the sequence was repeated to yield 1-benzyl 6-tert-butyl 6-azaspiro[2.5]octane-1,6-dicarboxylate (B-2). 1H NMR (400 MHz, CDCl3) δ 7.41-7.31 (m, 5H), 5.19-5.07 (m, 2H), 3.55-3.36 (m, 3H), 3.28-3.17 (m, 1H), 1.77-1.61 (m, 3H), 1.49-1.37 (m, 11H), 1.21 (t, J=4.9 Hz, 1H), 0.96 (dd, J=4.5, 7.6 Hz, 1H).

Step 2: (S)-1-benzyl 6-tert-butyl 6-azaspiro[2.5] octane-1,6-dicarboxylate (B-3)

Racemic 1-benzyl 6-tert-butyl 6-azaspiro[2.5]octane-1,6-dicarboxylate (B-2) was resolved on a ChiralPak AD column (300×50 mm) under supercritical fluid chromatography (SFC) conditions on a Thar 200 preparative SFC instrument. The racemate was dissolved isopropanol/DCM. The separation was accomplished using 20% MeOH/$CO_2$, flow rate 200 mL/min, 100 bar, 38° C. The 2nd peak is the S one.

Alternatively, the resolution could also be achieved using a mobile phase of 20% 1:1 heptane:ethanol/$CO_2$ on ChiralPak AY column (300×50 mm) with a flow rate of 200 mL/min. In that case the sample was prepared by dissolving in MeCN/ethanol. After separation, the fractions were dried off via rotary evaporator at bath temperature 40° C.

1H NMR-P1 (400 MHz, CDCl3) δ 7.42-7.29 (m, 5H), 5.19-5.06 (m, 2H), 3.55-3.35 (m, 3H), 3.26-3.16 (m, 1H), 1.75-1.59 (m, 3H), 1.53-1.33 (m, 11H), 1.21 (t, J=4.9 Hz, 1H), 0.96 (dd, J=4.6, 7.7 Hz, 1H).

1H NMR-P2 (400 MHz, CDCl3) δ 7.43-7.29 (m, 5H), 5.18-5.07 (m, 2H), 3.54-3.36 (m, 3H), 3.26-3.16 (m, 1H), 1.73-1.60 (m, 3H), 1.53-1.34 (m, 11H), 1.21 (t, J=5.1 Hz, 1H), 0.96 (dd, J=4.4, 7.9 Hz, 1H).

Step 3: (S)-6-(tert-butoxycarbonyl)-6-azaspiro[2.5] octane-1-carboxylic acid (B-4)

A mixture of (S)-1-benzyl 6-tert-butyl 6-azaspiro[2.5] octane-1,6-dicarboxylate (B-3, 5 g, 14.47 mmol), 10% Pd/C (0.154 g, 1.447 mmol) in MeOH (30 mL) was hydrogenated under $H_2$ (20 psi) at room temperature for 18 h. The mixture was filtered and the filter cake was washed with MeOH (30×3 mL). The filtrate was concentrated to dryness to give (S)-6-(tert-butoxycarbonyl)-6-azaspiro[2.5]octane-1-carboxylic acid (B-4), which was used without further purification. LCMS (ESI) calc'd for C13H21NO4 [M+H]+: 256.2, found: 200.1 (M−55).

Step 4: (S)-benzyl 6-azaspiro[2.5]octane-1-carboxylate (B-5)

TFA (15 mL, 202 mmol) was added to a stirred mixture of (S)-1-benzyl 6-tert-butyl 6-azaspiro[2.5]octane-1,6-dicarboxylate (B-3, 10.02 g, 29.0 mmol) in DCM (100 mL) at 0-5° C. and the mixture was stirred at room temperature for 4 h. All the volatiles were removed by evaporator to give crude (S)-benzyl 6-azaspiro[2.5]octane-1-carboxylate (B-5) which was used without further purification. LCMS (ESI) calc'd for C15H19NO2 [M+H]+: 246.3, found: 246.1.

Step 5: (S)-benzyl 6-methyl-6-azaspiro[2.5]octane-1-carboxylate (B-6)

Formaldehyde (18.77 g, 231 mmol) was added to a stirred mixture of (S)-benzyl 6-azaspiro[2.5]octane-1-carboxylate (B-5, 9.9 g, 28.9 mmol) in MeOH (100 mL) at room temperature and the mixture was stirred at room temperature for 2 h. Sodium triacetoxyhydroborate (18.39 g, 87 mmol) was added to the stirred mixture and the mixture was stirred at room temperature for 1 h. The solvent was removed by evaporator, then water (100 mL) was added and the mixture was extracted with ethyl acetate (50 mL) three times. The combined organic fractions were washed with aqueous NaHCO3 (saturated, 50 mL), dried (Na2SO4), filtered and the solvent was evaporated under reduced pressure. The residue was purified by silica gel column flash chromatography, eluting with DCM/MeOH=10/1 to give (S)-benzyl 6-methyl-6-azaspiro[2.5]octane-1-carboxylate (B-6). LCMS (ESI) calc'd for C16H21NO2 [M+H]+: 260.3, found: 260.1.

Step 6: (S)-6-methyl-6-azaspiro[2.5]octane-1-carboxylic acid (Intermediate B)

A solution of (S)-benzyl 6-methyl-6-azaspiro[2.5]octane-1-carboxylate (B-6, 7.5 g, 28.9 mmol) in MeOH (75 mL) was added to 100 mL three-necked bottle and then Pd/C (520 mg, 0.489 mmol) (10%, wet) was added under Ar. The suspension was degassed under vacuum and purged with N2 several times. The mixture was then stirred under H2 (15 psi) at 24° C. for 90 min. The mixture was filtered and the filter cake was washed with MeOH (20 mL×2). The filtrate was concentrated to dryness to give as (S)-6-methyl-6-azaspiro[2.5]octane-1-carboxylic acid (Intermediate B). 1H NMR (400 MHz, DMSO-d6) δ 2.95 (brs, 2H), 2.60 (s, 3H), 1.77-1.89 (m, 2H), 1.58 (t, J=6.6 Hz, 1H), 0.91-0.99 (m, 2H).

Intermediate C

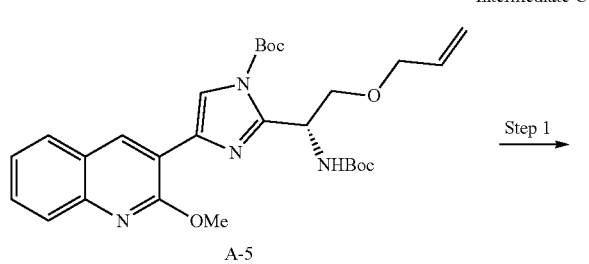

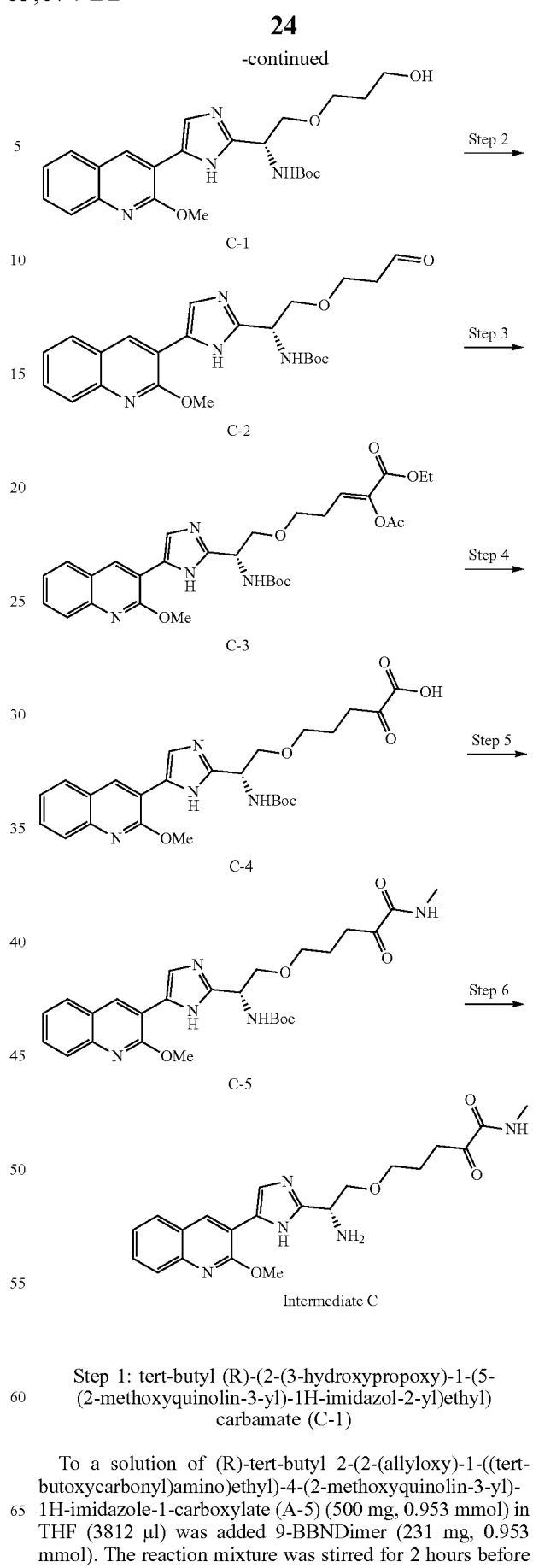

Step 1: tert-butyl (R)-(2-(3-hydroxypropoxy)-1-(5-(2-methoxyquinolin-3-yl)-1H-imidazol-2-yl)ethyl) carbamate (C-1)

To a solution of (R)-tert-butyl 2-(2-(allyloxy)-1-((tert-butoxycarbonyl)amino)ethyl)-4-(2-methoxyquinolin-3-yl)-1H-imidazole-1-carboxylate (A-5) (500 mg, 0.953 mmol) in THF (3812 μl) was added 9-BBNDimer (231 mg, 0.953 mmol). The reaction mixture was stirred for 2 hours before cooling to 0° C. To the reaction was added 1.0 M NaOH (1906 µl, 1.906 mmol) followed by 30% $H_2O_2$ (195 µl, 1.906 mmol) dropwise. The reaction mixture was stirred vigorously for 1 hour. The reaction mixture was extracted with EtOAc (5 mL×3), dried over $Na_2SO_4$ and concentrated. The residue was taken up in MeOH (1.19 mL)/THF (1.19 mL) and 3.0 M $K_2CO_3$ (475 µl, 1.425 mmol) was added. The reaction mixture was stirred for 2 hours before removing the volatiles and taking it up in EtOAc (10 mL) and $H_2O$ (10 mL). The mixture was extracted with EtOAc (10 mL×3), dried over $Na_2SO_4$ and concentrated. The residue was purified by column chromatography on silica (20-90% 3:1 EtOAc:EtOH/hexanes) to afford the title compound. MS: 443.3 (M+1).

Step 2: tert-butyl (R)-(1-(5-(2-methoxyquinolin-3-yl)-1H-imidazol-2-yl)-2-(3-oxopropoxy)ethyl)carbamate (C-2)

To a solution of (R)-tert-butyl (2-(3-hydroxypropoxy)-1-(5-(2-methoxyquinolin-3-yl)-1H-imidazol-2-yl)ethyl)carbamate (C-1) (320 mg, 0.723 mmol) in DCM (2411 µl) at ambient temperature was added DMP (322 mg, 0.759 mmol). The reaction mixture was stirred for 4 hours before quenching with $H_2O$ (5 mL), extracted with DCM (5 mL×3), dried over $Na_2SO_4$ and concentrated. The residue was purified by mass triggered reverse phase HPLC (MeCN/water with 0.1% TFA modifier) to afford the title compound. MS: 441.2 (M+1).

Step 3: ethyl (R,Z)-2-acetoxy-5-(2-((tert-butoxycarbonyl)amino)-2-(5-(2-methoxyquinolin-3-yl)-1H-imidazol-2-yl)ethoxy)pent-2-enoate (C-3)

To a solution of ethyl 2-acetoxy-2-(diethoxyphosphoryl)acetate (296 mg, 1.050 mmol) in THF (840 µl) at ambient temperature was added dried lithium chloride (44.5 mg, 1.050 mmol). The reaction mixture was stirred for 1 hour before cooling it to 0° C. and adding 1,1,3,3-tetramethylguanidine (132 µl, 1.050 mmol). After stirring the mixture for an additional 30 minutes, (R)-tert-butyl(1-(5-(2-methoxyquinolin-3-yl)-1H-imidazol-2-yl)-2-(3-oxopropoxy)ethyl)carbamate (C-2) (185 mg, 0.420 mmol) in THF (840 µl) was added dropwise and the reaction was warmed to ambient temperature. The mixture was stirred for 1 hour before it was quenched with a saturated solution of $NH_4Cl$ (5 mL), extracted with EtOAc (5 mL×3), dried over $Na_2SO_4$ and concentrated to afford the title compound. MS: 569.3 (M+1).

Step 4: (R)-5-(2-((tert-butoxycarbonyl)amino)-2-(5-(2-methoxyquinolin-3-yl)-1H-imidazol-2-yl)ethoxy)-2-oxopentanoic acid (C-4)

To a solution of (R,Z)-ethyl 2-acetoxy-5-(2-((tert-butoxycarbonyl)amino)-2-(5-(2-methoxyquinolin-3-yl)-1H-imidazol-2-yl)ethoxy)pent-2-enoate (C-3) (239 mg, 0.420 mmol) in EtOH (4200 µl) at ambient temperature was added 3.0M LiOH (700 µl, 2.100 mmol). The reaction mixture was stirred for 2 hours before it was quenched with a few drops of TFA. The mixture was purified by mass triggered reverse phase HPLC (MeCN/water with 0.1% TFA modifier) to afford the title compound. MS: 499.2 (M+1).

Step 5: tert-butyl (R)-(1-(5-(2-methoxyquinolin-3-yl)-1H-imidazol-2-yl)-2-((5-(methylamino)-4,5-dioxopentyl)oxy)ethyl)carbamate (C-5)

To a solution of (R)-5-(2-((tert-butoxycarbonyl)amino)-2-(5-(2-methoxyquinolin-3-yl)-1H-imidazol-2-yl)ethoxy)-2-oxopentanoic acid (C-4) (105 mg, 0.211 mmol) in DMF (2106 µl) at ambient temperature was added HATU (120 mg, 0.316 mmol) and DIPEA (73.6 µl, 0.421 mmol). The reaction mixture was stirred for 15 min and then methanamine (2.0 M in THF, 105 µl, 0.211 mmol) was added. The reaction mixture was stirred for 1 hour before quenching with a few drops of TFA. The mixture was purified by mass triggered reverse phase HPLC (MeCN/water with 0.1% TFA modifier) to afford the title compound. MS: 512.3 (M+1).

Step 6: (R)-5-(2-amino-2-(5-(2-methoxyquinolin-3-yl)-1H-imidazol-2-yl)ethoxy)-N-methyl-2-oxopentanamide (Intermediate C)

To a solution of (R)-tert-butyl (1-(5-(2-methoxyquinolin-3-yl)-1H-imidazol-2-yl)-2-((5-(methylamino)-4,5-dioxopentyl)oxy)ethyl)carbamate (C-5) (50 mg, 0.098 mmol) in dichloromethane (977 µl) at ambient temperature was added TFA (7.53 µl, 0.098 mmol). After stirring for 2 hours, the reaction mixture was concentrated and placed under vacuum. The residue was purified by mass triggered reverse phase HPLC (MeCN/water with 0.1% TFA modifier) to afford the title compound. MS: 412.2 (M+1).

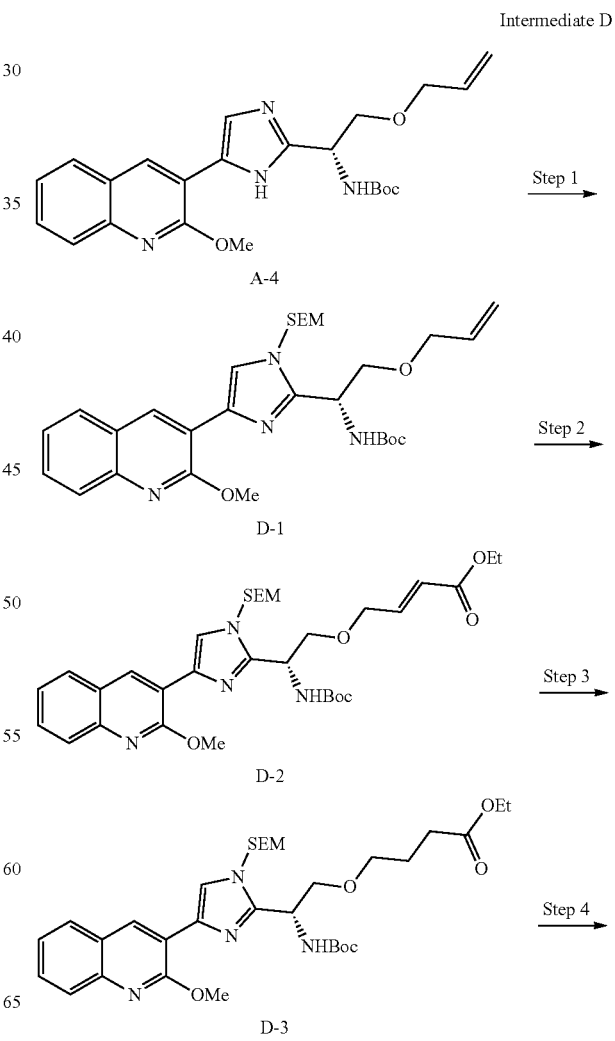

Intermediate D

-continued

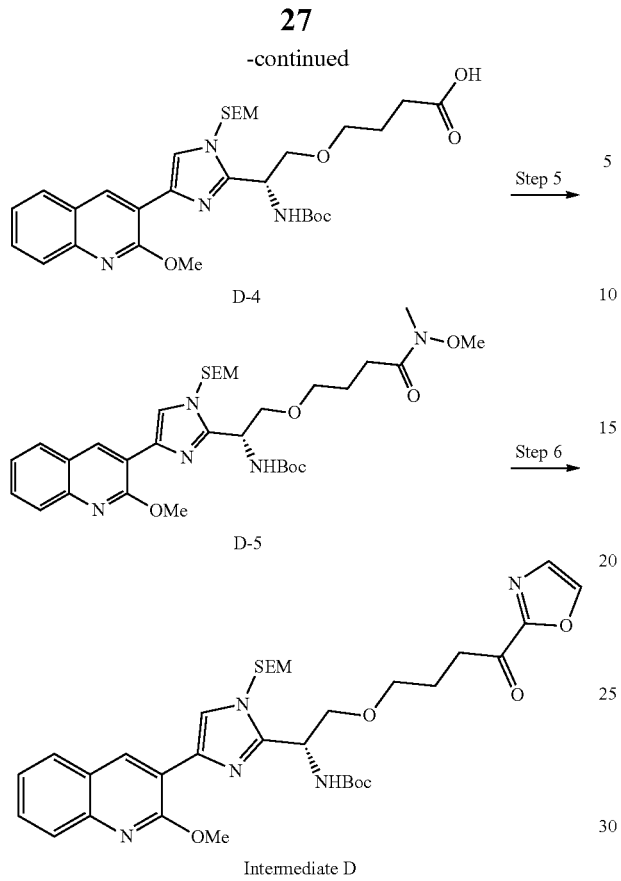

Intermediate D

Step 1: tert-butyl (R)-(2-(allyloxy)-1-(4-(2-methoxyquinolin-3-yl)-1-((2-(trimethylsilyl)ethoxy)methyl)-1H-imidazol-2-yl)ethyl)carbamate (D-1)

To a solution of (R)-tert-butyl(2-(allyloxy)-1-(5-(2-methoxyquinolin-3-yl)-1H-imidazol-2-yl)ethyl)carbamate (A-4) (4.00 g, 9.42 mmol) in DMF (47.1 ml) at 0° C. was added NaH (0.829 g, 20.73 mmol). The mixture was stirred for 30 min before adding SEM-Cl (1.838 ml, 10.37 mmol) and warming it to ambient temperature. After stirring for 2 hours, the mixture was quenched with H$_2$O (50 mL) and taken up in EtOAc (100 mL). The mixture was washed with H$_2$O (100 mL×2), dried over Na$_2$SO$_4$ and concentrated. The residue was purified by column chromatography on silica (5-70% 3:1 EtOAc:EtOH/hexanes) to afford the title compound. MS: 555.4 (M+1).

Step 2: ethyl (R,E)-4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)but-2-enoate (D-2)

To a solution of (R)-tert-butyl (2-(allyloxy)-1-(4-(2-methoxyquinolin-3-yl)-1-((2-(trimethylsilyl)ethoxy)methyl)-1H-imidazol-2-yl)ethyl)carbamate (D-1) (1000 mg, 1.803 mmol) in DCM (3605 µl) at ambient temperature was added ethyl acrylate (576 µl, 5.41 mmol) and Zhan catalyst-1B (66.1 mg, 0.090 mmol). The mixture was heated to 50° C. and stirred for 1 hour before cooling and concentrating. The residue was purified by column chromatography on silica (3-50% 3:1 EtOAc:EtOH/hexanes) to afford the title compound. MS: 627.4 (M+1).

Step 3: ethyl (R)-4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)butanoate (D-3)

To a solution of (R,E)-ethyl 4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)but-2-enoate (D-2) (1060 mg, 1.691 mmol) in MeOH (8455 µl) at ambient temperature was added Pd/C (180 mg, 0.169 mmol). A hydrogen balloon was added (vacuum purge 3×) and the mixture was stirred for 2 hours. The mixture was filtered through a pad of celite and concentrated to afford the title compound. MS: 629.4 (M+1).

Step 4: (R)-4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)butanoic acid (D-4)

To a solution of (R)-ethyl 4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)butanoate (D-3) (1.0 g, 1.590 mmol) in EtOH (15.90 ml) at ambient temperature was added 2.0 M lithium hydroxide (2.385 ml, 4.77 mmol). The reaction was stirred for 4 hours before concentrating. The crude residue was taken up in EtOAc (50 mL) and H$_2$O (50 mL), extracted with EtOAc (50 mL×2), dried over Na$_2$SO$_4$ and concentrated to afford the title compound. MS: 601.4 (M+1).

Step 5: tert-butyl (R)-(2-(4-(methoxy(methyl)amino)-4-oxobutoxy)-1-(4-(2-methoxyquinolin-3-yl)-1-((2-(trimethylsilyl)ethoxy)methyl)-1H-imidazol-2-yl)ethyl)carbamate (D-5)

To a mixture of (R)-4-(2-((tert-butoxycarbonyl)amino)-2-(4-(2-methoxyquinolin-3-yl)-1-((2-(trimethylsilyl)ethoxy)methyl)-1H-imidazol-2-yl)ethoxy)butanoic acid (D-4) (955 mg, 1.590 mmol) in DMF (7948 µl) at ambient temperature was added N,O-dimethylhydroxylamine hydrochloride (233 mg, 2.384 mmol), DIPEA (833 µl, 4.77 mmol), and HATU (665 mg, 1.749 mmol). The mixture was stirred for 2 hours before quenching with H$_2$O (20 mL), extracting with EtOAc (20 mL×3), drying over Na$_2$SO$_4$, and concentrating. The residue was purified by column chromatography on silica (5-100% 3:1 EtOAc:EtOH/hexanes) to afford the title compound. MS: 644.4 (M+1).

Step 6: tert-butyl (R)-(1-(4-(2-methoxyquinolin-3-yl)-1-((2-(trimethylsilyl)ethoxy)methyl)-1H-imidazol-2-yl)-2-(4-(oxazol-2-yl)-4-oxobutoxy)ethyl)carbamate (Intermediate D)

To a mixture of oxazole (279 µl, 4.24 mmol) in THF (4 mL) at 0° C. was added isopropylmagnesium chloride (2120 µl, 4.24 mmol) dropwise. The mixture was stirred for 30 minutes before adding it to a separate flask containing (R)-tert-butyl (1-(4-(2-methoxyquinolin-3-yl)-1-((2-(trimethylsilyl)ethoxy)methyl)-1H-imidazol-2-yl)-2-(4-(oxazol-2-yl)-4-oxobutoxy)ethyl)carbamate (D-5) (803 mg, 1.232 mmol) in THF (9423 µl) at 0° C. The reaction was stirred for 2 hours before warming it to room temp. After 2 hours the mixture was heated to 50° C. for 5 hours. The mixture was cooled and quenched with a saturated solution of NH$_4$Cl (20 mL), extracted with EtOAc (20 mL×3), dried over Na$_2$SO$_4$, and concentrated. The residue was purified by column chromatography on silica (5-100% 3:1 EtOAc:EtOH/hexanes) to afford the title compound. MS: 652.4 (M+1).

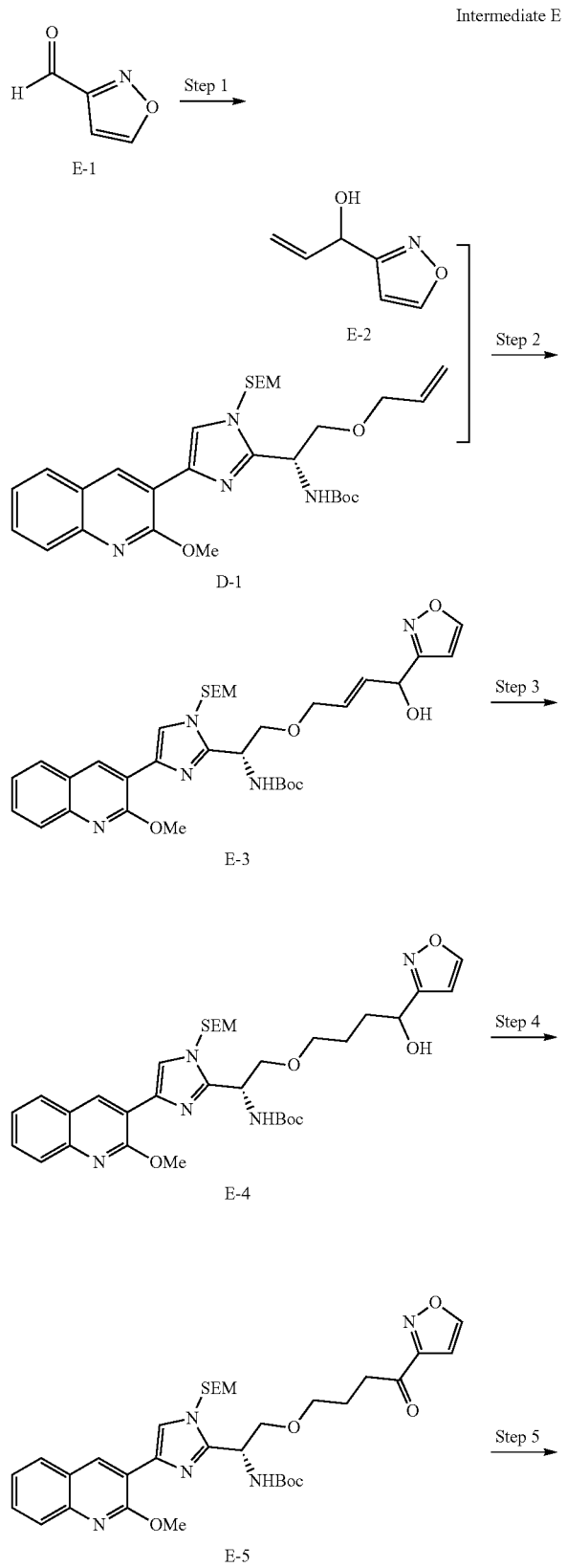

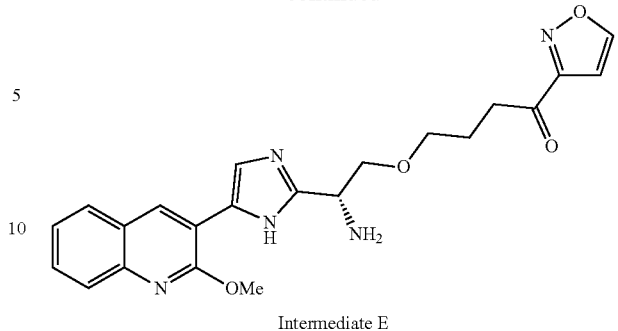

Intermediate E

Step 1: 1-(isoxazol-3-yl)prop-2-en-1-ol (E-2)

To a solution of isoxazole-3-carbaldehyde (E-1) (3.42 g, 35.2 mmol) in THF (160 ml)/Ether (100 ml) at 0° C. was added vinylmagnesium bromide (70.5 ml, 70.5 mmol) in THF. The mixture was stirred for 2 hours before quenching with 2 M HCl (100 mL). The mixture was washed with $H_2O$ (200 mL), brine (200 mL), dried over $Na_2SO_4$ and concentrated. The residue was purified by column chromatography on silica (2-80% 3:1 EtOAc:EtOH/hexanes) to afford the title compound. NMR: (500 MHz, Chloroform-d) δ 8.38 (s, 1H), 6.37 (s, 1H), 6.10 (ddd, J=16.4, 10.2, 5.7 Hz, 1H), 5.46 (d, J=17.2 Hz, 2H), 5.32 (d, J=10.3 Hz, 1H).

Step 2: tert-butyl ((1R)-2-(((E)-4-hydroxy-4-(isoxazol-3-yl)but-2-en-1-yl)oxy)-1-(4-(2-methoxyquinolin-3-yl)-1-((2-(trimethylsilyl)ethoxy)methyl)-1H-imidazol-2-yl)ethyl)carbamate (E-3)

To a mixture of (R)-tert-butyl (2-(allyloxy)-1-(4-(2-methoxyquinolin-3-yl)-1-((2-(trimethylsilyl)ethoxy)methyl)-1H-imidazol-2-yl)ethyl)carbamate (D-1) (500 mg, 0.901 mmol) in toluene (1803 µl) at ambient temperature was added 1-(isoxazol-3-yl)prop-2-en-1-ol (E-2) (226 mg, 1.803 mmol) followed by M71-S1Pr (74.1 mg, 0.090 mmol). The mixture was heated to 60° C. for 3 hours before cooling and concentrating. The residue was purified by column chromatography on silica (2-80% 3:1 EtOAc:EtOH/hexanes) to afford the title compound. MS: 652.5 (M+1).

Step 3: tert-butyl (1R)-2-(4-hydroxy-4-(isoxazol-3-yl)butoxy)-1-(4-(2-methoxyquinolin-3-yl)-1-((2-(trimethylsilyl)ethoxy)methyl)-1H-imidazol-2-yl)ethyl)carbamate (E-4)

To a mixture of tert-butyl ((1R)-2-(((E)-4-hydroxy-4-(isoxazol-3-yl)but-2-en-1-yl)oxy)-1-(4-(2-methoxyquinolin-3-yl)-1-((2-(trimethylsilyl)ethoxy)methyl)-1H-imidazol-2-yl)ethyl)carbamate (E-3) (160 mg, 0.245 mmol) in MeOH (2455 µl) at ambient temperature was added Pd—C (13.06 mg, 0.012 mmol). A hydrogen balloon was added (vacuum purge 3×) and the mixture was stirred for 30 min. The mixture was filtered through a pad of celite and concentrated to afford the title compound. MS: 654.5 (M+1).

Step 4: tert-butyl (R)-(2-(4-(isoxazol-3-yl)-4-oxobutoxy)-1-(4-(2-methoxyquinolin-3-yl)-1-((2-(trimethylsilyl)ethoxy)methyl)-1H-imidazol-2-yl)ethyl)carbamate (E-5)

To a mixture of tert-butyl ((1R)-2-(4-hydroxy-4-(isoxazol-3-yl)butoxy)-1-(4-(2-methoxyquinolin-3-yl)-1-((2-

(trimethylsilyl)ethoxy)methyl)-1H-imidazol-2-yl)ethyl)carbamate (E-4) (160 mg, 0.245 mmol) in DCM (2447 µl) at ambient temperature was added DMP (114 mg, 0.269 mmol). The mixture was stirred for 2 hours before concentrating. The residue was purified by column chromatography on silica (2-80% 3:1 EtOAc:EtOH/hexanes) to afford the title compound. MS: 652.5 (M+1).

Step 5: (R)-4-(2-amino-2-(5-(2-methoxyquinolin-3-yl)-1H-imidazol-2-yl)ethoxy)-1-(isoxazol-3-yl)butan-1-one (Intermediate E)

To a mixture of (R)-tert-butyl (2-(4-(isoxazol-3-yl)-4-oxobutoxy)-1-(4-(2-methoxyquinolin-3-yl)-1-((2-(trimethylsilyl)ethoxy)methyl)-1H-imidazol-2-yl)ethyl)carbamate (E-5) (100 mg, 0.153 mmol) in DCM (1534 µl) at ambient temperature was added TFA (118 µl, 1.534 mmol). The mixture was heated to 50° C. for 5 hours before concentrating to afford the title compound. MS: 422.3 (M+1).

Intermediate F

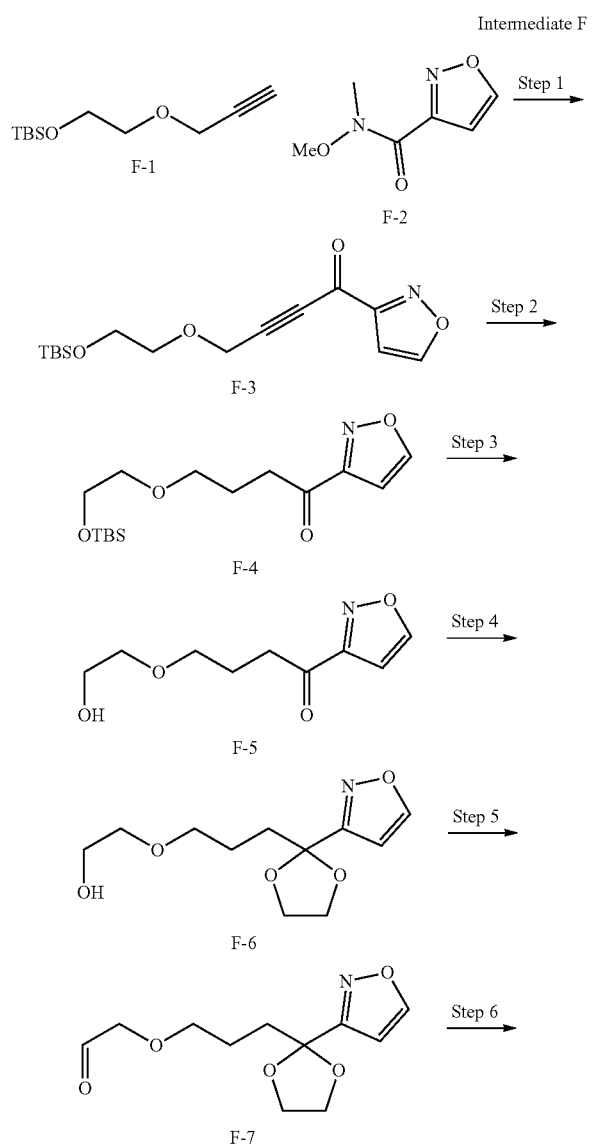

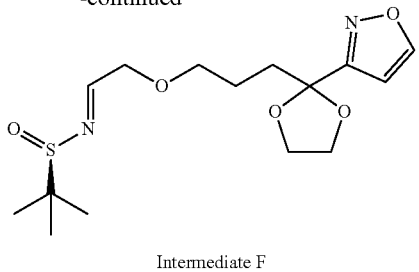

Intermediate F

Step 1: 4-(2-((tert-butyldimethylsilyl)oxy)ethoxy)-1-(isoxazol-3-yl) but-2-yn-1-one (F-3)

To a mixture of tert-butyldimethyl(2-(prop-2-yn-1-yloxy)ethoxy)silane (F-1) (10.57 g, 49.3 mmol) in THF (90 ml) at −78° C. was added nBuLi (2.5 M in hexanes, 19.73 ml, 49.3 mmol) dropwise. The mixture was stirred for 30 minutes before adding N-methoxy-N-methylisoxazole-3-carboxamide (F-2) (7.0 g, 44.8 mmol) in THF (10.0 mL) dropwise. The mixture was stirred for an additional 1 hr before quenching with 4.0 M HCl (100 mL). The mixture was warmed to room temperature, extracted with EtOAc (150 mL×3), dried over $Na_2SO_4$ and concentrated to afford the title compound. MS: 310.3 (M+1).

Step 2: 4-(2-((tert-butyldimethylsilyl)oxy)ethoxy)-1-(isoxazol-3-yl)butan-1-one (F-4)

To a suspension of Pd/C (2.385 g, 2.241 mmol) in MeOH (112 ml) at ambient temperature was added 4-(2-((tert-butyldimethylsilyl)oxy)ethoxy)-1-(isoxazol-3-yl)but-2-yn-1-one (F-3) (13.87 g, 44.8 mmol). A balloon of hydrogen was added (vacuum purge 3×) and the mixture was allowed to stir for 2.5 hour. The mixture was filtered through a pad of celite and the filtrate was concentrated to afford the title compound. MS: 314.3 (M+1).

Step 3: 4-(2-hydroxyethoxy)-1-(isoxazol-3-yl)butan-1-one (F-5)

To a mixture of 4-(2-((tert-butyldimethylsilyl)oxy)ethoxy)-1-(isoxazol-3-yl)butan-1-one (F-4) (14.05 g, 44.8 mmol) in THF (90 ml) at ambient temperature was added TBAF (1.0 M in THF, 44.8 ml, 44.8 mmol). The mixture was allowed to stir for 2 hours before concentrating. The residue was purified by column chromatography on silica (5-90% 3:1 EtOAc:EtOH/hexanes) to afford the title compound. MS: 200.2 (M+1).

Step 4: 2-(3-(2-(isoxazol-3-yl)-1,3-dioxolan-2-yl)propoxy)ethan-1-ol (F-6)

To a mixture of 4-(2-hydroxyethoxy)-1-(isoxazol-3-yl)butan-1-one (F-5) (5.95 g, 29.9 mmol) in toluene (149 ml) at ambient temperature was added ethylene glycol (16.66 ml, 299 mmol) and PPTS (0.375 g, 1.493 mmol). A Dean-Stark trap was added and the mixture was heated to 130° C. for 16 hours. The mixture was cooled and concentrated. The resulting residue was taken up in EtOAc (250 mL), washed with a sat'd solution of $NaHCO_3$ (250 mL), dried over $Na_2SO_4$ and concentrated to afford the title compound. MS: 244.2 (M+1).

Step 5: 2-(3-(2-(isoxazol-3-yl)-1,3-dioxolan-2-yl)propoxy)acetaldehyde (F-7)

To a mixture of 2-(3-(2-(isoxazol-3-yl)-1,3-dioxolan-2-yl)propoxy)ethanol (F-6) (5.90 g, 24.25 mmol) in DCM (44.1 ml)/DMSO (29.4 ml) at 0° C. was added DIPEA (12.71 ml, 72.8 mmol) and pyridine sulfur trioxide (5.79 g, 36.4 mmol). The mixture was stirred for 2 hours before quenching with H$_2$O (200 mL) and taken up in EtOAc (250 mL). The mixture was washed with H$_2$O (200 mL), 1 M HCl (200 mL), saturated solution of NaHCO$_3$(200 mL), dried over Na$_2$SO$_4$ and concentrated. The residue was purified by column chromatography on silica (2-60% 3:1 EtOAc:EtOH/hexanes) to afford the title compound. MS: 242.2 (M+1).

Step 6: (R,E)-N-(2-(3-(2-(isoxazol-3-yl)-1,3-dioxolan-2-yl)propoxy)ethylidene)-2-methylpropane-2-sulfinamide (Intermediate F)

To a mixture of 2-(3-(2-(isoxazol-3-yl)-1,3-dioxolan-2-yl)propoxy)acetaldehyde (F-7) (2.55 g, 10.57 mmol) in DCM (32.0 ml) at ambient temperature was added copper (II) sulfate (3.37 g, 21.14 mmol) and (R)-2-methylpropane-2-sulfinamide (1.409 g, 11.63 mmol). The mixture was stirred overnight before filtering through a pad of celite. The filtrate was concentrated. The residue was purified by column chromatography on silica (5-100% EtOAc/hexanes) to afford the title compound. MS: 345.3 (M+1).

Intermediate G

G-1

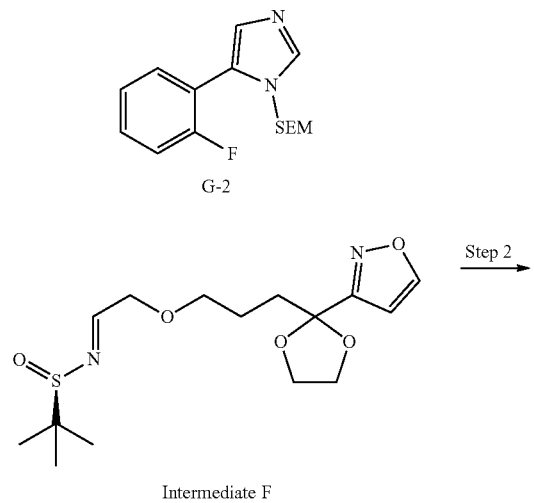

Intermediate F

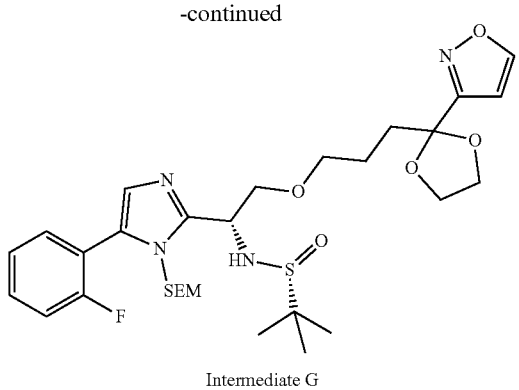

Intermediate G

Step 1: 5-(2-fluorophenyl)-1-((2-(trimethylsilyl)ethoxy)methyl)-1H-imidazole (G-2)

To a solution of 4-bromo-1H-imidazole (G-1) (log, 68.0 mmol) in DMF (100 ml) at 0° C. was added sodium hydride (3 g, 75 mmol). After stirring for 1 hour at 0° C., 2-(trimethylsilyl)ethoxymethyl chloride (12 g, 72.0 mmol) in THF (50 ml) was added before stirring overnight at room temp. The mixture was cooled to 0° C., before adding ice (10 g) and H$_2$O (200 ml) and extracting with EtOAc (500 ml). The organic layer was separated, dried (MgSO$_4$), then filtered before the solvent was evaporated to yield crude Sem Protected bromo imidazole. To this was added (2-fluorophenyl)boronic acid (14 g, 100 mmol), [1,1'-bis(diphenylphosphino)ferrocene]dichloropalladium(II) (2 g, 2.73 mmol), and potassium carbonate (11 g, 80 mmol) dissolved in dioxane (200 ml) and water (20 ml). The reaction was degassed and stirred at 90° C. overnight. The mixture was cooled, concentrated, and extracted with EtOAc (500 ml×2) and H$_2$O (200 ml×2), washed with brine, dried (MgSO$_4$), filtered, and concentrated. The residue was purified by column chromatography on silica (50% DCM/hexanes, then 50% EtOAc/hexanes) to afford the title compound. MS: 293.0 (M+1).

Step 2: (R)—N—((R)-1-(5-(2-fluorophenyl)-1-((2-(trimethylsilyl)ethoxy)methyl)-1H-imidazol-2-yl)-2-(3-(2-(isoxazol-3-yl)-1,3-dioxolan-2-yl)propoxy)ethyl)-2-methylpropane-2-sulfinamide (G-3)

To a mixture of 5-(2-fluorophenyl)-1-((2-(trimethylsilyl)ethoxy)methyl)-1H-imidazole (G-2) (1.274 g, 4.36 mmol) in THF (8.80 ml) at −78° C. was added nBuLi (2.5 M in hexanes, 1.510 ml, 3.77 mmol). The mixture was stirred for 20 minutes before adding (R,E)-N-(2-(3-(2-(isoxazol-3-yl)-1,3-dioxolan-2-yl)propoxy)ethylidene)-2-methylpropane-2-sulfinamide (INTERMEDIATE F) (1.00 g, 2.90 mmol) in THF (1 mL) dropwise. The mixture was stirred for 30 minutes before quenching with a saturated solution of NH$_4$Cl (25 mL). The mixture was warmed to room temp, extracted with EtOAc (25 mL×3), dried over Na$_2$SO$_4$ and concentrated. The residue was purified by column chromatography on silica (5-95% 3:1 EtOAc:EtOH/hexanes) to afford the title compound. MS: 637.5 (M+1).

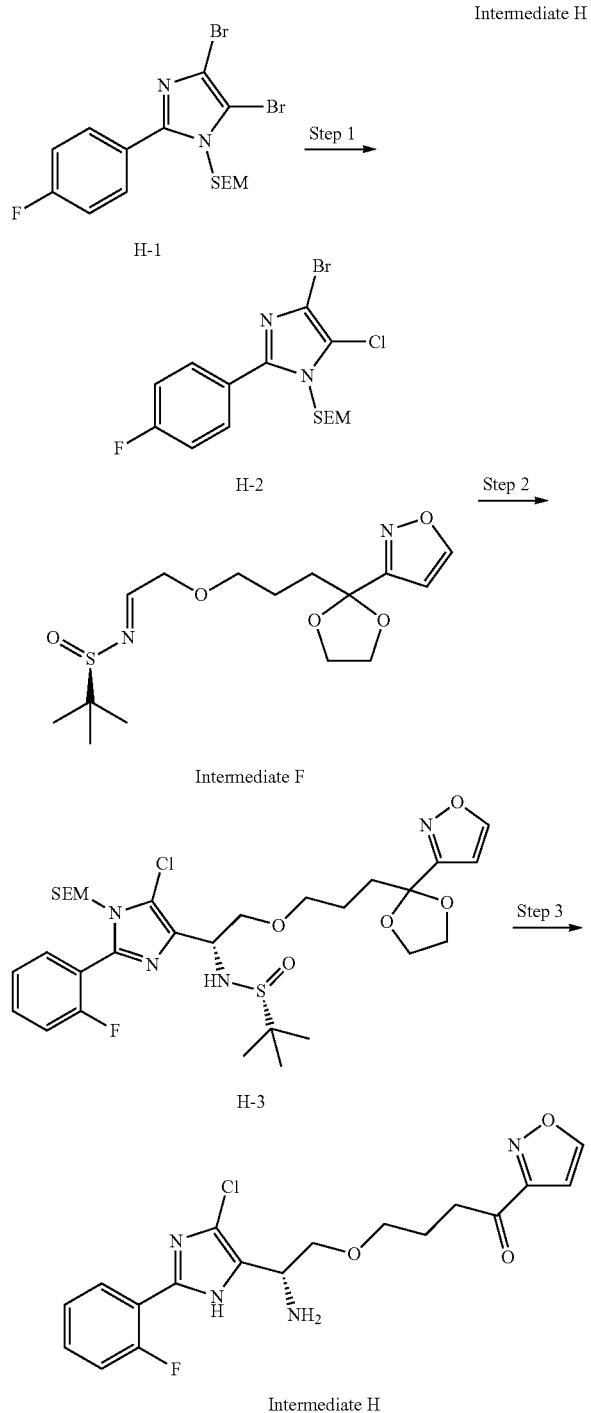

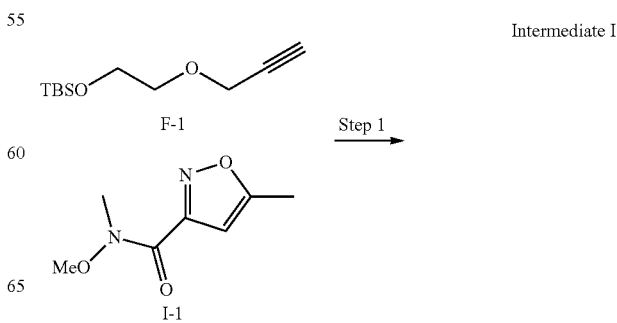

hexanes, 8.44 ml, 21.10 mmol) dropwise. The mixture stirred for 20 min before adding perchloroethane (6.49 g, 27.4 mmol) dissolved in THF (10 mL) dropwise. The mixture stirred for 1 hour before quenching with a saturated solution of NH4Cl (100 mL) and warmed to ambient temperature. The mixture was taken up in EtOAc (100 mL) and water (100 mL), extracted with EtOAc (200 mL×3), dried over Na₂SO₄, and concentrated. The residue was purified by column chromatography on silica (2-70% 3:1 EtOAc:EtOH/hexanes) to afford the title compound. MS: 407.2, 409.2 (M+1).

Step 2: (R)—N—((R)-1-(5-chloro-2-(2-fluorophenyl)-1-((2-(trimethylsilyl)ethoxy)methyl)-1H-imidazol-4-yl)-2-(3-(2-(isoxazol-3-yl)-1,3-dioxolan-2-yl)propoxy)ethyl)-2-methylpropane-2-sulfinamide (H-3)

To a mixture of 4-bromo-5-chloro-2-(4-fluorophenyl)-1-((2-(trimethylsilyl)ethoxy)methyl)-1H-imidazole (H-2) (1.626 g, 4.01 mmol) in THF (13.36 ml) at −78° C. was added nBuLi (2.5 M in hexanes, 1.469 ml, 3.67 mmol) dropwise. The mixture was stirred for 20 min before adding it to a separate flask containing (R,E)-N-(2-(3-(2-(isoxazol-3-yl)-1,3-dioxolan-2-yl)propoxy)ethylidene)-2-methylpropane-2-sulfinamide (INTERMEDIATE F) (1.15 g, 3.34 mmol) dissolved in THF (6 mL) at −78° C. The mixture was stirred for 1 hour before quenching with a saturated solution of NH₄Cl (10 mL) and it was warmed to ambient temperature. The mixture was taken up in EtOAc (10 mL) and water (10 mL), extracted with EtOAc (20 mL×3), dried over Na₂SO₄ and concentrated. The residue was purified by column chromatography on silica (2-70% 3:1 EtOAc:EtOH/hexanes) to afford the title compound. MS: 671.5 (M+1).

Step 3: (R)-4-(2-amino-2-(4-chloro-2-(2-fluorophenyl)-1H-imidazol-5-yl)ethoxy)-1-(isoxazol-3-yl)butan-1-one (Intermediate H)

To a mixture of (R)—N—((R)-1-(5-chloro-2-(4-fluorophenyl)-1-((2-(trimethylsilyl)ethoxy)methyl)-1H-imidazol-4-yl)-2-(3-(2-(isoxazol-3-yl)-1,3-dioxolan-2-yl)propoxy)ethyl)-2-methylpropane-2-sulfinamide (H-3)(1.25 g, 1.862 mmol) in MeOH (9.31 ml) at ambient temperature was added 6.0 M HCl (1.862 ml, 11.17 mmol). The mixture was heated to 50° C. and stirred overnight. The mixture was concentrated. The residue was purified by column chromatography on C18 (5-95% MeCN/water with 0.1% TFA modifier) to afford the title compound. MS: 393.3 (M+1).

Step 1: 4-bromo-5-chloro-2-(4-fluorophenyl)-1-((2-(trimethylsilyl)ethoxy)methyl)-1H-imidazole (H-2)

To a mixture of 4,5-dibromo-2-(4-fluorophenyl)-1-((2-(trimethylsilyl)ethoxy)methyl)-1H-imidazole (H-1) (9.50 g, 21.10 mmol) (Huang, Z.; Jin, J.; Machajewski, T. D.; Antonios-McCrea, W. R.; McKenna, M.; Poon, D.; Renhowe, P. A.; Sendzik, M.; Shafer, C. M.; Smith, A.; Xu, Y.; Zhang, Q., PCT Int. Appl., 2009115572, 24 Sep. 2009) in THF (106 ml) at −78° C. was added nBuLi (2.5 M in

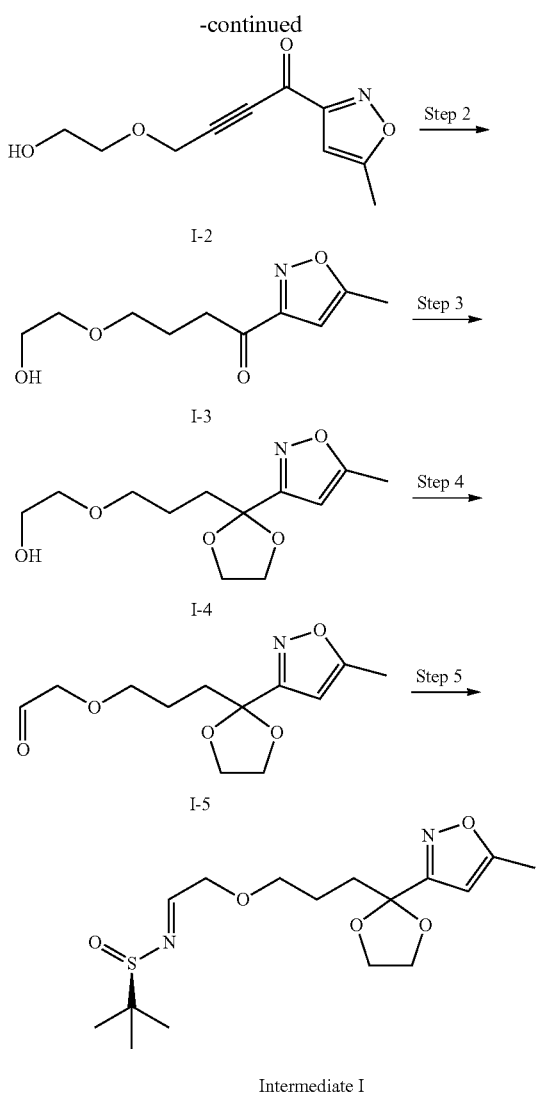

Intermediate I

Step 1: 4-(2-hydroxyethoxy)-1-(5-methylisoxazol-3-yl)but-2-yn-1-one (I-2)

To a mixture of tert-butyldimethyl(2-(prop-2-yn-1-yloxy)ethoxy)silane (F-1) (6.93 g, 32.3 mmol) at −78° C. was added nBuLi (2.5 M in hexanes, 12.93 ml, 32.3 mmol). The mixture was stirred for 30 minutes before adding N-methoxy-N,5-dimethylisoxazole-3-carboxamide (I-1) (5 g, 29.4 mmol) in THF (6.0 mL) dropwise. The mixture was stirred for an additional 1 hr before quenching with 4.0 M HCl (100 mL). The mixture was warmed to room temperature, extracted with EtOAc (150 mL×3), dried over Na$_2$SO$_4$, and concentrated to afford the title compound. MS: 210.1 (M+1).

Step 2: 4-(2-hydroxyethoxy)-1-(5-methylisoxazol-3-yl)butan-1-one (I-3)

To a suspension of Pd/C (1.564 g, 1.470 mmol) in MeOH (100 ml) at ambient temperature was added 4-(2-hydroxyethoxy)-1-(5-methylisoxazol-3-yl)but-2-yn-1-one (I-2) (6.15 g, 29.4 mmol). A balloon of hydrogen was added (vacuum purge 3×) and the mixture was allowed to stir for 2.5 hours. The mixture was filtered through a pad of celite and the filtrate was concentrated. The residue was purified by column chromatography on silica (5-100% 3:1 EtOAc:EtOH/hexanes) to afford the title compound. MS: 214.2 (M+1).

Step 3: 2-(3-(2-(5-methylisoxazol-3-yl)-1,3-dioxolan-2-yl)propoxy)ethan-1-ol (I-4)

To a mixture of 4-(2-hydroxyethoxy)-1-(5-methylisoxazol-3-yl)butan-1-one (I-3) (2.25 g, 10.55 mmol) in toluene (52.8 ml) at ambient temperature was added ethylene glycol (5.88 ml, 106 mmol) and PPTS (0.133 g, 0.528 mmol). A Dean-Stark trap was added and the mixture was heated to 130° C. for 16 hours. The mixture was cooled and concentrated. The resulting residue was taken up in EtOAc (250 mL), washed with a sat'd solution of NaHCO$_3$(250 mL), dried over Na$_2$SO$_4$, and concentrated to afford the title compound.

Step 4: 2-(3-(2-(5-methylisoxazol-3-yl)-1,3-dioxolan-2-yl)propoxy)acetaldehyde (I-5)

To a mixture of 2-(3-(2-(5-methylisoxazol-3-yl)-1,3-dioxolan-2-yl)propoxy)ethanol (I-4) (2.88 g, 11.19 mmol) in DCM (20.43 ml)/DMSO (13.49 ml) at 0° C. was added DIPEA (5.87 ml, 33.6 mmol) and pyridine sulfur trioxide (2.67 g, 16.79 mmol). The mixture stirred for 2 hours before quenching with H$_2$O (200 mL) and taking up in EtOAc (250 mL). It was washed with H$_2$O (200 mL), 1 M HCl (200 mL), a saturated solution of NaHCO$_3$(200 mL), dried over Na$_2$SO$_4$ and concentrated. The residue was purified by column chromatography on silica (2-60% 3:1 EtOAc:EtOH/hexanes) to afford the title compound.

Step 5: (R,E)-2-methyl-N-(2-(3-(2-(5-methylisoxazol-3-yl)-1,3-dioxolan-2-yl)propoxy)ethylidene)propane-2-sulfinamide (Intermediate I)

To a mixture of 2-(3-(2-(5-methylisoxazol-3-yl)-1,3-dioxolan-2-yl)propoxy)acetaldehyde (I-5) (1.0022 g, 3.93 mmol) in DCM (11.90 ml) was added copper(II) sulfate (1.253 g, 7.85 mmol) and (R)-2-methylpropane-2-sulfinamide (0.523 g, 4.32 mmol). The solution was stirred overnight at ambient temperature. The mixture was filtered through a pad of celite before concentrating. The residue was purified by column chromatography on silica (2-60% 3:1 EtOAc:EtOH/hexanes) to afford the title compound. NMR: (500 MHz, Chloroform-d) δ 8.10-8.15 (m, 1H), 5.95 (s, 1H), 4.30-4.35 (m, 2H), 3.95-4.10 (m, 4H), 3.55-3.60 (m, 2H), 2.40 (s, 3H), 2.10-2.15 (m, 2H), 1.45-1.55 (m, 2H), 1.15-1.25 (m, 9H).

Intermediate J

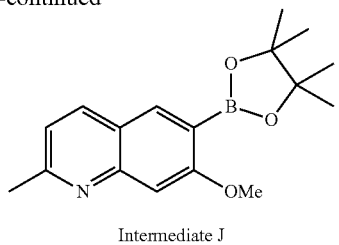

Intermediate J

Step 1: 6-bromo-7-methoxy-2-methylquinoline (J-2)

A suspension of 4-bromo-3-methoxyaniline (J-1) (15.00 g, 74.2 mmol) and HCl (52.5 mL, 639 mmol) in water (60 mL) was heated to 110° C. (E)-but-2-enal (8.23 g, 117 mmol) was added dropwise into the mixture over 30 min. The reaction mixture was stirred at 110° C. for another 2 h. The reaction mixture was combined with another reaction with the same scale. The combined mixture was cooled to rt, aqueous ammonia (28%, 300 mL) was added and the mixture was extracted with ethyl acetate (200×3 mL). The combined organic fractions were washed with brine (400 mL), dried over Na$_2$SO$_4$, filtered and the solvent was evaporated under reduced pressure. The residue was purified by silica gel column flash chromatography, eluting with petroleum ether/EtOAc=10%-40% to give 6-bromo-7-methoxy-2-methylquinoline (J-2). LCMS (ESI) calc'd for C11H10BrNO [M+H]+: 252.0, found: 251.9.

Step 2: 7-methoxy-2-methyl-6-(4,4,5,5-tetramethyl-1,3,2-dioxaborolan-2-yl)quinoline (Intermediate J)

PdCl$_2$(dppf) (85 mg, 0.116 mmol) was added to a stirred mixture of potassium acetate (405 mg, 4.13 mmol), BPD (786 mg, 3.09 mmol) and 6-bromo-7-methoxy-2-methylquinoline (J-2, 520 mg, 2.063 mmol) in 1,4-dioxane (8 mL) at room temperature and the mixture was stirred at 80° C. for 12 h under N$_2$ protection. The mixture was concentrated and the residue was purified by silica gel column flash chromatography, eluting with petroleum ether/EtOAc=1:1 to give 7-methoxy-2-methyl-6-(4,4,5,5-tetramethyl-1,3,2-dioxaborolan-2-yl)quinoline (Intermediate J). LCMS (ESI) calc'd for C17H22BNO3 [M+H]+: 300.2, found: 300.2. 1H NMR (400 MHz, CDCl3) δ 8.12 (s, 1H), 7.98 (d, J=8.22 Hz, 1H), 7.34 (s, 1H), 7.14 (d, J=8.22 Hz, 1H), 3.97 (s, 3H), 2.72 (s, 3H), 1.41 (s, 12H).

Intermediate K

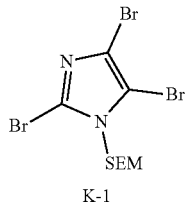

K-1

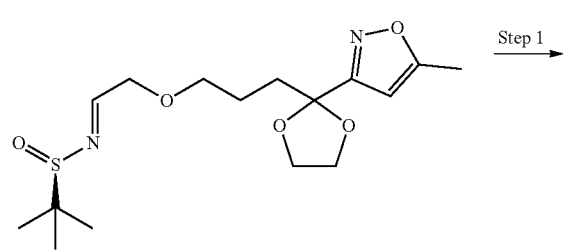

Intermediate I

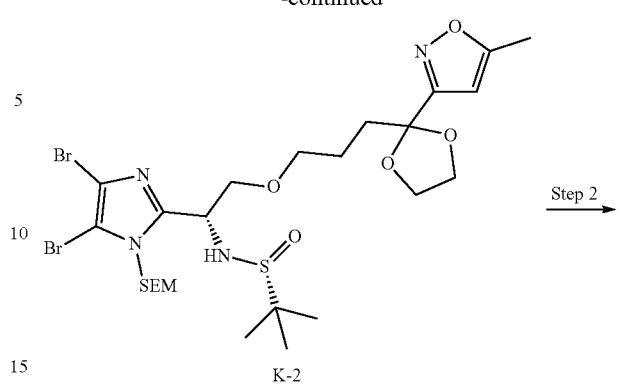

K-2

Step 2

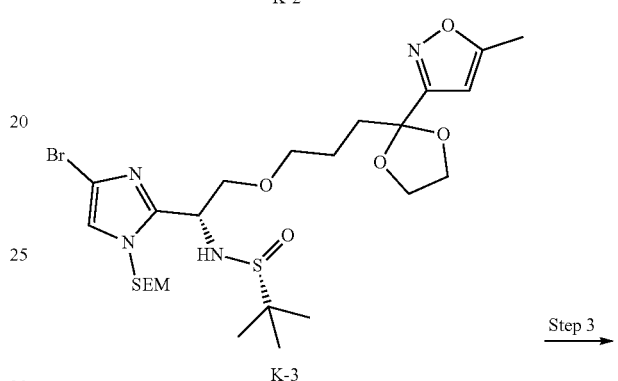

K-3

Step 3

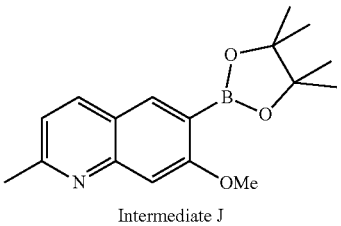

Intermediate J

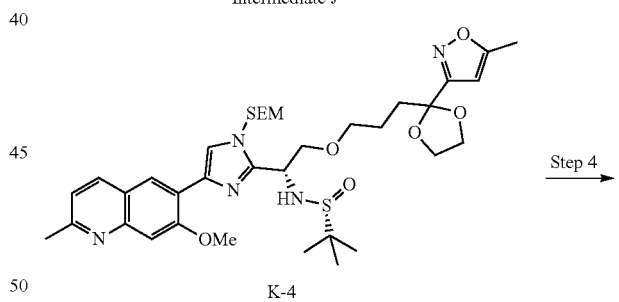

K-4

Step 4

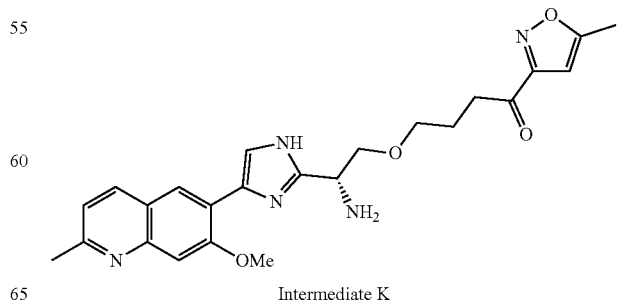

Intermediate K

Step 1: (R)—N—((R)-1-(4,5-dibromo-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-2)

To a flask containing 2,4,5-tribromo-1-((2-(trimethylsilyl)ethoxy)methyl)-1H-imidazole (K-1) (1467 mg, 3.37 mmol) in THF (1.30E+04 μl) at −78° C. was added nBuLi (2.5 M in hexanes, 1349 μl, 3.37 mmol) dropwise. The mixture was stirred for about 5 minutes and then (R,E)-2-methyl-N-(2-(3-(2-(5-methylisoxazol-3-yl)-1,3-dioxolan-2-yl)propoxy)ethylidene)propane-2-sulfinamide (INTERMEDIATE I) (930 mg, 2.59 mmol) was added dropwise to the solution. The reaction was stirred for 1 hour and was then quenched with H₂O (20 mL) before warming to ambient temperature. The product was extracted using EtOAc (20 mL×3), dried over Na₂SO₄ and concentrated. The residue was purified by column chromatography on silica (5-100% 3:1 EtOAc:EtOH/hexanes) to afford the title compound. MS: 715.4 (M+1).

Step 2: (R)—N—((R)-1-(4-bromo-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-3)

To a vial containing (R)—N—((S)-1-(4,5-dibromo-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-2) (668 mg, 0.935 mmol) in THF (4674 μl) at −78° C. under nitrogen, nBuLi (2.5 M in hexanes, 748 μl, 1.870 mmol) was added dropwise. The reaction was stirred for 30 minutes before it was quenched with iPrOH (720 μl, 9.35 mmol). The mixture was quenched with a saturated solution of NH₄Cl (20 mL), warmed to ambient temperature, extracted with EtOAc (20 mL×3), dried over Na₂SO₄ and concentrated. The residue was purified by column chromatography on silica (5-100% 3:1 EtOAc:EtOH/hexanes) to afford the title compound. MS: 637.4 (M+1).

Step 3: (R)—N—((R)-1-(4-(7-methoxy-2-methylquinolin-6-yl)-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-4)

7-methoxy-2-methyl-6-(4,4,5,5-tetramethyl-1,3,2-dioxaborolan-2-yl)quinoline (INTERMEDIATE J) (296 mg, 0.990 mmol) was added to a vial containing (R)—N—((S)-1-(4-bromo-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-3) (314.6 mg, 0.495 mmol) dissolved in dioxane (1980 μl). Tripotassium phosphate (263 mg, 1.237 mmol) was dissolved in water (495 μl) and transferred into the reaction vial. XPhos Palladium G3 (20.95 mg, 0.025 mmol) was added to the mixture and the reaction was stirred at 100° C. for 2 hours. The mixture was cooled and water (10 mL) was added. It was extracted with EtOAc (10 mL×3), dried over Na₂SO₄ and concentrated to afford the title compound. MS: 728.6 (M+1).

Step 4: (R)-4-(2-amino-2-(4-(7-methoxy-2-methylquinolin-6-yl)-1H-imidazol-2-yl)ethoxy)-1-(5-methylisoxazol-3-yl)butan-1-one (Intermediate K)

(R)—N—((R)-1-(4-(7-methoxy-2-methylquinolin-6-yl)-1-((2-(trimethylsilyl)ethoxy)methyl)-1H-imidazol-2-yl)-2-(3-(2-(5-methylisoxazol-3-yl)-1,3-dioxolan-2-yl)propoxy)ethyl)-2-methylpropane-2-sulfinamide (K-4) (360 mg, 0.495 mmol) was dissolved in MeOH (2473 μl). 6.0 M HCl (659 μl, 3.96 mmol) was added to the mixture and it was heated to 50° C. and stirred overnight before concentrating. The residue was purified by column chromatography on C18 (5-95% MeCN/water with 0.1% TFA modifier) to afford the title compound. MS: 450.4 (M+1).

Intermediate L

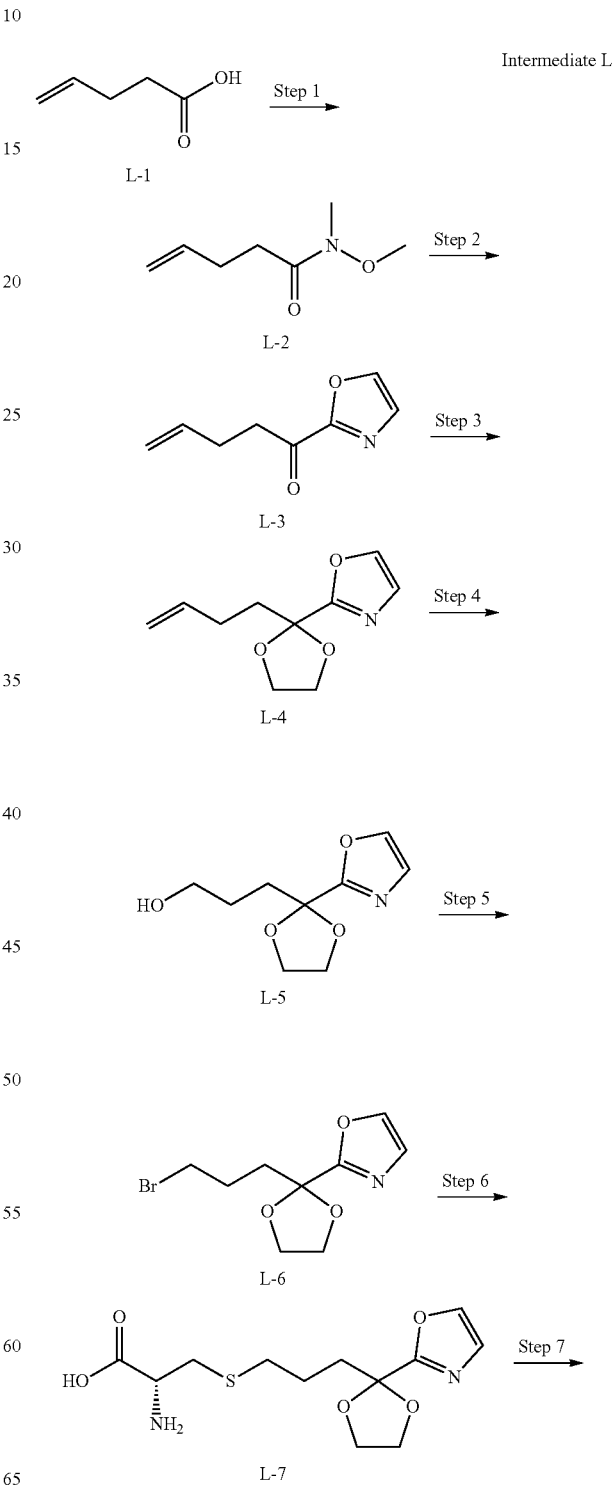

43

-continued

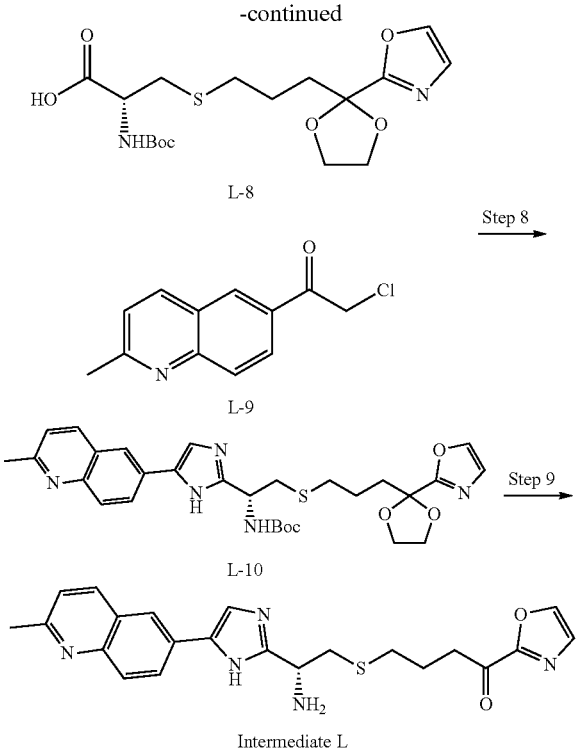

L-8

Step 8 →

L-9

L-10

Intermediate L

Step 1: N-methoxy-N-methylpent-4-enamide (L-2)

Oxalyl chloride (5.25 ml, 59.9 mmol) was added to the solution of DMF (0.046 ml, 0.599 mmol) and pent-4-enoic acid (L-1, 3.00 g, 30.0 mmol) in DCM (50 ml), and the resultant mixture was stirred at 25° C. for 2 h. The reaction mixture was poured to a stirred solution of N,O-dimethyl-hydroxylamine hydrochloride (9.75 g, 0.10 mol) in water (30 mL) at 0° C., and stirred for 1 h. The reaction mixture was separated and the organic layer was washed with brine (30 mL) and dried. The solvent was removed in vacuo to give N-methoxy-N-methylpent-4-enamide (L-2) which was used to the next step without further purification. 1H NMR (400 MHz, CDCl3) δ 5.86 (m, 1H), 5.06 (d, J=19.6 Hz, 1H), 4.98 (d, J=10.0 Hz, 1H), 3.8 (s, 3H), 3.17 (s, 3H), 2.46-2.60 (m, 2H), 2.35-2.40 (m, 2H).

Step 2: 1-(oxazol-2-yl)pent-4-en-1-one (L-3)

To a solution of oxazole (0.904 g, 13.10 mmol) in THF (15 ml) was added drop wise isopropylmagnesium chloride (6.55 ml, 13.10 mmol) at −15° C. The resultant mixture was stirred at −15° C. for 40 min, then a solution of N-methoxy-N-methylpent-4-enamide (L-2, 1.50 g, 10.48 mmol) in THF (5 mL) was added to the reaction mixture, and it was stirred at room temperature for 16 h. The mixture was quenched with aqueous NH4Cl (saturated, 10 mL), and the mixture was extracted with ethyl acetate (15×2 mL). The combined organic fractions were washed with brine (saturated, 10 mL), dried (Na2SO4), filtered and the solvent was evaporated under reduced pressure. The residue was purified by silica gel flash chromatography (ISCORF75; Sepa flash column), eluting with petroleum ether/EtOAc=20:1-5:1 to give 1-(oxazol-2-yl)pent-4-en-1-one (L-3). 1H NMR (400 MHz, CDCl3) δ 7.76 (s, 1H), 7.27 (s, 1H), 5.81 (m, 1H), 4.90-5.08 (m, 2H), 3.13 (t, J=7.43 Hz, 3H), 2.45 (q, J=6.78 Hz, 3H).

44

Step 3: 2-(2-(but-3-en-1-yl)-1,3-dioxolan-2-yl)oxa-zole (L-4)

P-toluenesulfonic acid monohydrate (0.094 g, 0.496 mmol) was added to a stirred mixture of 1-(oxazol-2-yl)pent-4-en-1-one (L-3) (1.5 g, 9.92 mmol) and ethane-1,2-diol (11 mL, 198 mmol) in toluene (40 mL) at 15° C., and the mixture was stirred at 130° C. for 8 h. The mixture was cooled, and the solvent was evaporated under reduced pressure to get the crude. The crude product was purified by flash silica gel chromatography (ISCO®; 20 g SepaFlash® Silica Flash Column, Eluent of 0~10% EtOAc/Petroleum ether gradient @ 40 mL/min) to give 2-(2-(but-3-en-1-yl)-1,3-dioxolan-2-yl)oxazole (L-4). 1H NMR (400 MHz, chloroform-d) δ 7.63 (d, J=0.7 Hz, 1H), 7.09 (d, J=0.7 Hz, 1H), 5.91-5.74 (m, 1H), 5.06-4.93 (m, 2H), 4.16-4.09 (m, 5H), 2.29-2.17 (m, 5H).

Step 4: 3-(2-(oxazol-2-yl)-1,3-dioxolan-2-yl)propan-1-ol (L-5)

Osmium tetroxide (0.15 mL, 0.015 mmol) was added to a stirred mixture of 2-(2-(but-3-en-1-yl)-1,3-dioxolan-2-yl)oxazole (L-4) (100 mg, 0.512 mmol), 2,6-dimethylpyridine (110 mg, 1.025 mmol), sodium periodate (438 mg, 2.049 mmol) in a co-solvent dioxane (3 mL) and water (1 mL) at 18° C., and the mixture was stirred at 18° C. for 3 h. The mixture was quenched with water (10 mL), extracted with EtOAc (10 mL*3), the combined organic layers were washed with brine (10 mL), dried over Na2SO4, filtered and concentrated to get the 3-(2-(oxazol-2-yl)-1,3-dioxolan-2-yl)propanal which was used in the next step directly. LCMS (ESI) calc'd for C9H11NO4 [M+H]+: 198.1, found: 198.0, tR=0.301 min.

NaBH4 (273 mg, 7.23 mmol) was added to a stirred mixture of 3-(2-(oxazol-2-yl)-1,3-dioxolan-2-yl)propanal (950 mg, 4.82 mmol) in MeOH (10 mL) at 20° C. and the mixture was stirred at 20° C. for 1 h. The mixture was quenched with water (10 mL), extracted with EtOAc (10 mL*3), the combined organic layers were washed with brine (10 mL), dried over Na2SO4, filtered and concentrated to get the crude. The crude product with was purified by flash silica gel chromatography (ISCO®; 20 g SepaFlash® Silica Flash Column, Eluent of 0~10% EtOAc/Petroleum ether gradient @ 40 mL/min) to give 3-(2-(oxazol-2-yl)-1,3-dioxolan-2-yl)propan-1-ol (L-5). 1H NMR (400 MHz, chloroform-d) δ 7.64 (s, 1H), 7.10 (s, 1H), 4.19-4.10 (m, 5H), 3.68 (t, J=6.3 Hz, 2H), 2.31-2.24 (m, 2H), 1.80-1.66 (m, 3H).

Step 5: 2-(2-(3-bromopropyl)-1,3-dioxolan-2-yl)oxazole (L-6)

PPh3 (1053 mg, 4.02 mmol) was added to a stirred mixture of 3-(2-(oxazol-2-yl)-1,3-dioxolan-2-yl)propan-1-ol (L-5) (400 mg, 2.008 mmol), CBr4 (1332 mg, 4.02 mmol) in DCM (10 mL) at 20° C., and the mixture was stirred at 20° C. for 2 h. The mixture was quenched with water (10 mL), extracted with EtOAc (10 mL*3), the combined organic layers were washed with brine (10 mL), dried over Na2SO4, filtered and concentrated to get the crude. The crude product was purified by flash silica gel chromatography (ISCOr; 20 g SepaFlashr Silica Flash Column, Eluent of 0~10% EtOAc/Petroleum ether gradient @ 40 mL/min) to give 2-(2-(3-bromopropyl)-1,3-dioxolan-2-yl)oxazole (L-6). 1H NMR (400 MHz, chloroform-d) δ 7.64 (d, J=0.9 Hz, 1H), 7.10 (d, J=0.7 Hz, 1H), 4.20-4.07 (m, 5H), 3.46 (t, J=6.7 Hz, 2H), 2.36-2.25 (m, 2H), 2.10-2.00 (m, 2H).

Step 6: (R)-2-amino-3-((3-(2-(oxazol-2-yl)-1,3-dioxolan-2-yl)propyl)thio)propanoic acid (L-7)

2-(2-(3-bromopropyl)-1,3-dioxolan-2-yl)oxazole (L-6) (410 mg, 1.564 mmol) was added to a stirred mixture of (R)-2-amino-3-mercaptopropanoic acid (193 mg, 1.596 mmol) in ethanol (3 ml) and NaOH (3.5 mL, 7.00 mmol) at 20° C., and the mixture was stirred at 20° C. for 15 h. The mixture was used in the next step directly. LCMS (ESI) calc'd for C12H18N2O5S [M+H]+: 303.1, found: 303.0, tR=0.201 min.

Step 7: (R)-2-((tert-butoxycarbonyl)amino)-3-((3-(2-(oxazol-2-yl)-1,3-dioxolan-2-yl)propyl)thio)propanoic acid (L-8)

BOC$_2$O (730 μl, 3.18 mmol) was added to a stirred mixture of (R)-2-amino-3-((3-(2-(oxazol-2-yl)-1,3-dioxolan-2-yl)propyl)thio)propanoic acid (480 mg, 1.588 mmol) at 18° C., and the mixture was stirred at 18° C. for 45 min. LCMS (ESI) calc'd for C17H26N2O7S [M+H]+: 403.1, found: 403.2, tR=1.345 min, the mixture was quenched with water (10 mL), extracted with EtOAc (10 mL*3), the combined organic layers were washed with brine (10 mL), dried over Na$_2$SO$_4$, filtered and concentrated to get the crude. The crude product was purified by flash silica gel chromatography (ISCO®; 20 g SepaFlash® Silica Flash Column, Eluent of 0~10% EtOAc/Petroleum ether gradient @ 40 mL/min) to give (R)-2-((tert-butoxycarbonyl)amino)-3-((3-(2-(oxazol-2-yl)-1,3-dioxolan-2-yl)propyl)thio)propanoic acid (L-8). 1H NMR (400 MHz, chloroform-d) δ 7.64 (s, 1H), 7.11 (s, 1H), 5.78-5.61 (m, 1H), 4.35-4.22 (m, 1H), 4.10 (s, 4H), 3.15-2.94 (m, 1H), 2.94-2.78 (m, 1H), 2.57 (t, J=7.0 Hz, 2H), 2.27-2.13 (m, 2H), 2.05 (s, 3H), 1.69 (quin, J=7.4 Hz, 2H), 1.48-1.45 (m, 2H), 1.42 (s, 13H), 1.26 (t, J=7.1 Hz, 4H).

Step 8: (R)-tert-butyl (1-(5-(2-methylquinolin-6-yl)-1H-imidazol-2-yl)-2-((3-(2-(oxazol-2-yl)-1,3-dioxolan-2-yl)propyl)thio)ethyl)carbamate (L-10)

DIPEA (0.4 mL, 2.497 mmol) was added to the solution of (R)-2-((tert-butoxycarbonyl)amino)-3-((3-(2-(oxazol-2-yl)-1,3-dioxolan-2-yl)propyl)thio)propanoic acid (L-8) (670 mg, 1.665 mmol) and 2-chloro-1-(2-methylquinolin-6-yl)ethanone (L-9) (402 mg, 1.831 mmol) in DMF (10 mL), and the resultant mixture was stirred at 25° C. for 5 h. The mixture was quenched with aqueous NH$_4$Cl (saturated, 10 mL), and the mixture was extracted with ethyl acetate (3×30 mL). The combined organic fractions were washed with brine (saturated, 15 mL), dried (Na$_2$SO$_4$), filtered and the solvent was evaporated under reduced pressure to give the crude. The crude product was purified by flash silica gel chromatography (ISCO®; 20 g SepaFlash® Silica Flash Column, Eluent of 0-10% EtOAc/Petroleum ether gradient @ 40 mL/min) to give (R)-2-(2-methylquinolin-6-yl)-2-oxoethyl 2-((tert-butoxycarbonyl)amino)-3-((3-(2-(oxazol-2-yl)-1,3-dioxolan-2-yl)propyl)thio)propanoate. 1H NMR (400 MHz, chloroform-d) δ 8.37 (d, J=1.6 Hz, 1H), 8.19-8.12 (m, 2H), 8.09 (s, 1H), 7.68-7.55 (m, 1H), 7.38 (d, J=8.4 Hz, 1H), 7.07 (s, 1H), 5.63-5.41 (m, 3H), 4.72-4.63 (m, 1H), 4.14-4.06 (m, 4H), 3.20-3.10 (m, 1H), 3.09-3.00 (m, 1H), 2.78 (s, 3H), 2.64 (s, 2H), 2.31-2.18 (m, 2H), 1.81-1.70 (m, 2H), 1.45 (s, 9H).

Acetic acid, ammonia salt (197 mg, 2.56 mmol) was added to the solution of (R)-2-(2-methylquinolin-6-yl)-2-oxoethyl 2-((tert-butoxycarbonyl)amino)-3-((3-(2-(oxazol-2-yl)-1,3-dioxolan-2-yl)propyl)thio)propanoate (500 mg, 0.854 mmol) in toluene (5 mL), and the resultant mixture was stirred at 110° C. for 4 h. The mixture was concentrated in vacuo. The residue was purified by silica gel flash chromatography (ISCORF75; Sepa flash column), eluting with petroleum ether/EtOAc=10:1-1:2 to give (R)-tert-butyl (1-(5-(2-methylquinolin-6-yl)-1H-imidazol-2-yl)-2-((3-(2-(oxazol-2-yl)-1,3-dioxolan-2-yl)propyl)thio)ethyl)carbamate (L-10). 1H NMR (400 MHz, chloroform-d) δ 8.24-8.19 (m, 1H), 8.10-8.04 (m, 1H), 8.01 (s, 2H), 7.63 (s, 1H), 7.37 (s, 1H), 7.10 (s, 1H), 5.72 (brs, 1H), 4.90 (d, J=7.3 Hz, 1H), 4.17-4.08 (m, 5H), 3.30-3.15 (m, 1H), 3.13-3.03 (m, 1H), 2.75 (s, 3H), 2.70-2.54 (m, 2H), 2.43-2.29 (m, 1H), 2.26-2.13 (m, 1H), 1.80 (s, 2H), 1.47 (s, 10H).

Step 9: (R)-4-((2-amino-2-(5-(2-methylquinolin-6-yl)-1H-imidazol-2-yl)ethyl)thio)-1-(oxazol-2-yl)butan-1-one (Intermediate L)

HCl (0.5 mL, 6.09 mmol) was added to a stirred mixture of (R)-tert-butyl (1-(5-(2-methylquinolin-6-yl)-1H-imidazol-2-yl)-2-((3-(2-(oxazol-2-yl)-1,3-dioxolan-2-yl)propyl)thio)ethyl)carbamate (L-10) (220 mg, 0.389 mmol) in MeOH (4 mL) at 20° C. and the mixture was stirred at 20° C. for 15 h. LCMS (ESI) calc'd for C22H23N5O2S [M+H]+: 422.2, found: 422.2, tR=0.517 min showed the target was formed and 25% de-Boc product was remained. The mixture was concentrated to get (R)-4-((2-amino-2-(5-(2-methylquinolin-6-yl)-1H-imidazol-2-yl)ethyl)thio)-1-(oxazol-2-yl)butan-1-one (Intermediate L).

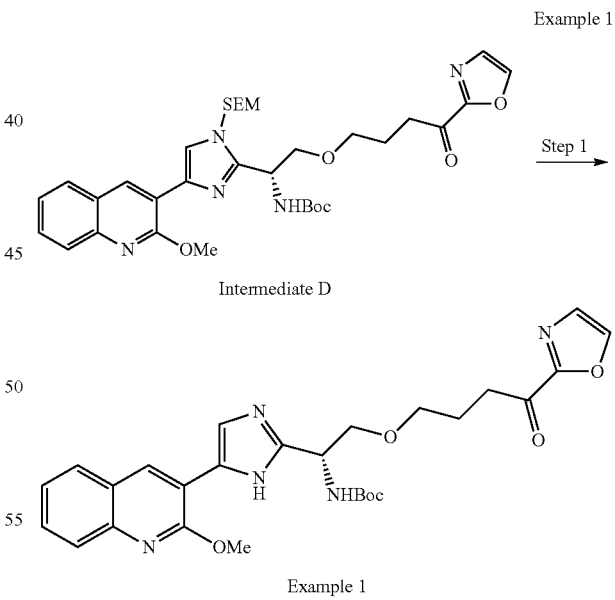

Example 1

Step 1: (R)-4-(2-amino-2-(5-(2-methoxyquinolin-3-yl)-1H-imidazol-2-yl)ethoxy)-1-(oxazol-2-yl)butan-1-one (Example 1)

To a solution of (R)-tert-butyl (1-(4-(2-methoxyquinolin-3-yl)-1-((2-(trimethylsilyl)ethoxy)methyl)-1H-imidazol-2-yl)-2-(4-(oxazol-2-yl)-4-oxobutoxy)ethyl)carbamate (Intermediate D) (800 mg, 1.227 mmol) in DCM (3068 µl) at ambient temperature was added TFA (946 µl, 12.27 mmol). The mixture was stirred for 4 hours before concentrating. The residue was purified by column chromatography on C18 (5-100% MeCN/water with 0.1% TFA modifier) to afford the title compound. MS: 422.3 (M+1). 1H NMR (500 MHz, DMSO-d6) δ 8.75 (s, 1H), 8.60 (s, 2H), 8.36 (s, 1H), 7.87 (d, J=8.0 Hz, 1H), 7.78 (d, J=7.3 Hz, 2H), 7.62 (t, J=7.6 Hz, 1H), 7.48 (s, 1H), 7.44 (t, J=7.5 Hz, 1H), 4.64 (s, 1H), 4.13 (s, 3H), 3.86 (d, J=5.8 Hz, 2H), 3.62-3.47 (m, 2H), 3.10 (t, J=7.2 Hz, 2H), 1.88 (p, J=6.9 Hz 2H).

Example 2

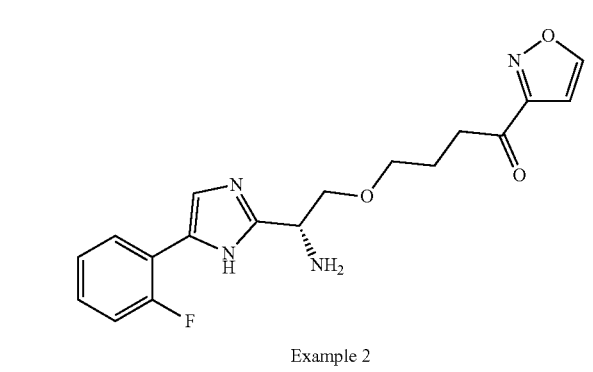

Intermediate G

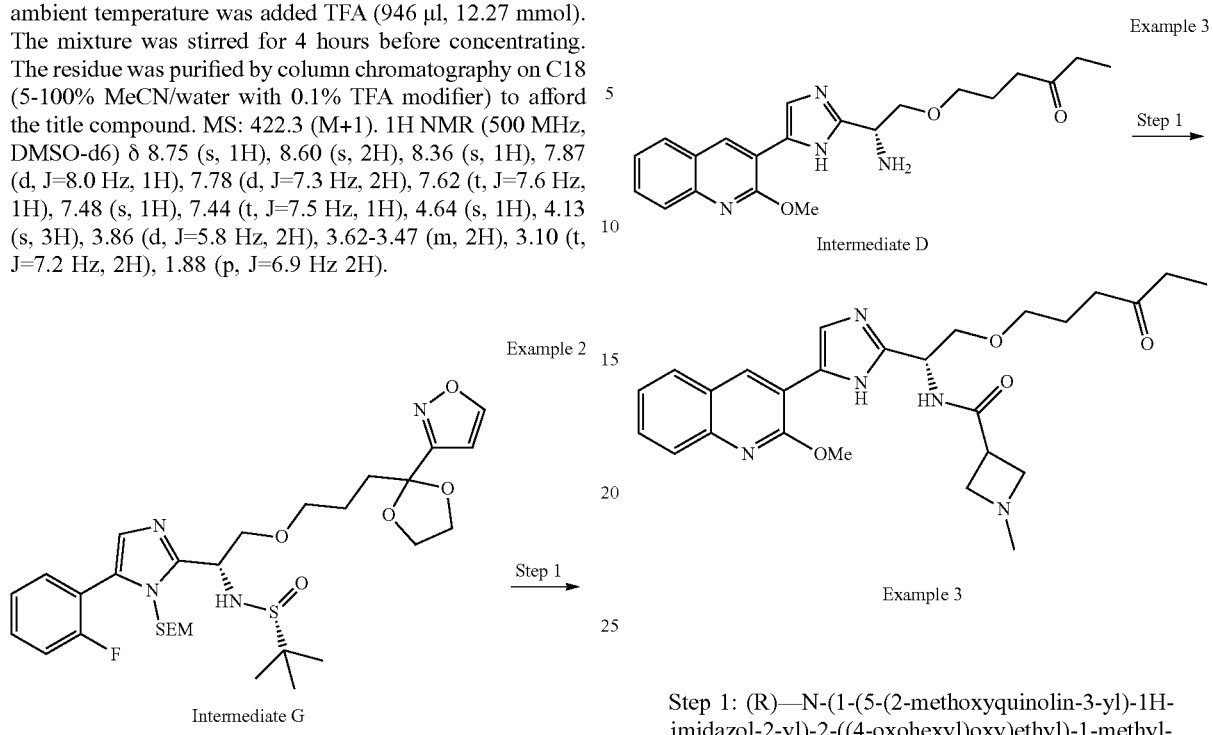

Example 2

Step 1: (R)-4-(2-amino-2-(5-(2-fluorophenyl)-1H-imidazol-2-yl)ethoxy)-1-(isoxazol-3-yl)butan-1-one (Example 2)

To a mixture of (R)—N—((R)-1-(5-(2-fluorophenyl)-1-((2-(trimethylsilyl)ethoxy)methyl)-1H-imidazol-2-yl)-2-(3-(2-(isoxazol-3-yl)-1,3-dioxolan-2-yl)propoxy)ethyl)-2-methylpropane-2-sulfinamide (Intermediate G) (330 mg, 0.518 mmol) in MeOH (1570 µl) at ambient temperature was added 6.0 M HCl (518 µl, 3.11 mmol). The mixture was heated to 50° C. for 16 hours before concentrating. The residue was purified by column chromatography on C18 (5-95% MeCN/water with 0.1% TFA modifier) to afford the title compound. MS: 359.3 (M+1). 1H NMR (500 MHz, DMSO-d6) δ 9.12 (s, 1H), 8.54 (s, 2H), 8.02 (s, 1H), 7.53 (d, J=3.6 Hz, 1H), 7.20-7.30 (m, 2H), 6.90 (s, 1H), 4.60 (s, 1H), 3.82 (d, J=5.9 Hz, 2H), 3.53 (ddd, J=22.5, 9.6, 4.8 Hz, 2H), 3.11 (t, J=7.2 Hz, 2H), 1.89 (p, J=6.8 Hz, 2H).

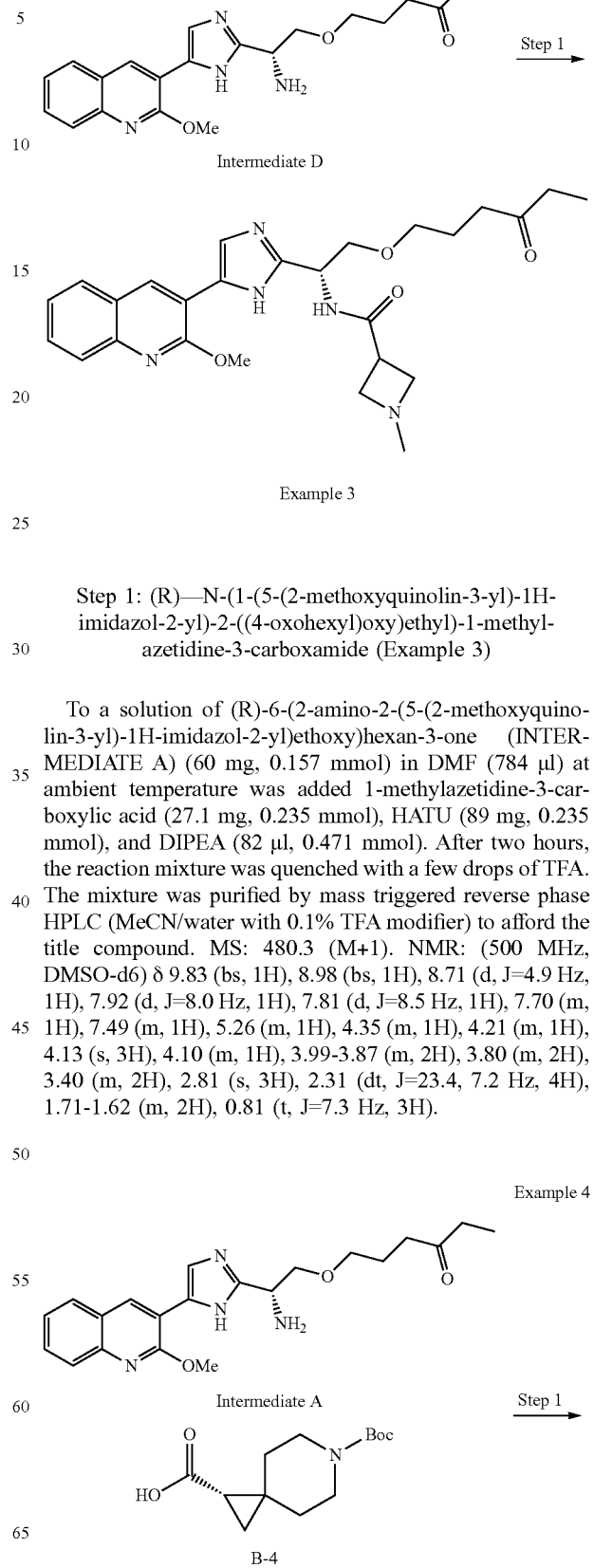

Step 1: (R)—N-(1-(5-(2-methoxyquinolin-3-yl)-1H-imidazol-2-yl)-2-((4-oxohexyl)oxy)ethyl)-1-methyl-azetidine-3-carboxamide (Example 3)

To a solution of (R)-6-(2-amino-2-(5-(2-methoxyquinolin-3-yl)-1H-imidazol-2-yl)ethoxy)hexan-3-one (INTERMEDIATE A) (60 mg, 0.157 mmol) in DMF (784 µl) at ambient temperature was added 1-methylazetidine-3-carboxylic acid (27.1 mg, 0.235 mmol), HATU (89 mg, 0.235 mmol), and DIPEA (82 µl, 0.471 mmol). After two hours, the reaction mixture was quenched with a few drops of TFA. The mixture was purified by mass triggered reverse phase HPLC (MeCN/water with 0.1% TFA modifier) to afford the title compound. MS: 480.3 (M+1). NMR: (500 MHz, DMSO-d6) δ 9.83 (bs, 1H), 8.98 (bs, 1H), 8.71 (d, J=4.9 Hz, 1H), 7.92 (d, J=8.0 Hz, 1H), 7.81 (d, J=8.5 Hz, 1H), 7.70 (m, 1H), 7.49 (m, 1H), 5.26 (m, 1H), 4.35 (m, 1H), 4.21 (m, 1H), 4.13 (s, 3H), 4.10 (m, 1H), 3.99-3.87 (m, 2H), 3.80 (m, 2H), 3.40 (m, 2H), 2.81 (s, 3H), 2.31 (dt, J=23.4, 7.2 Hz, 4H), 1.71-1.62 (m, 2H), 0.81 (t, J=7.3 Hz, 3H).

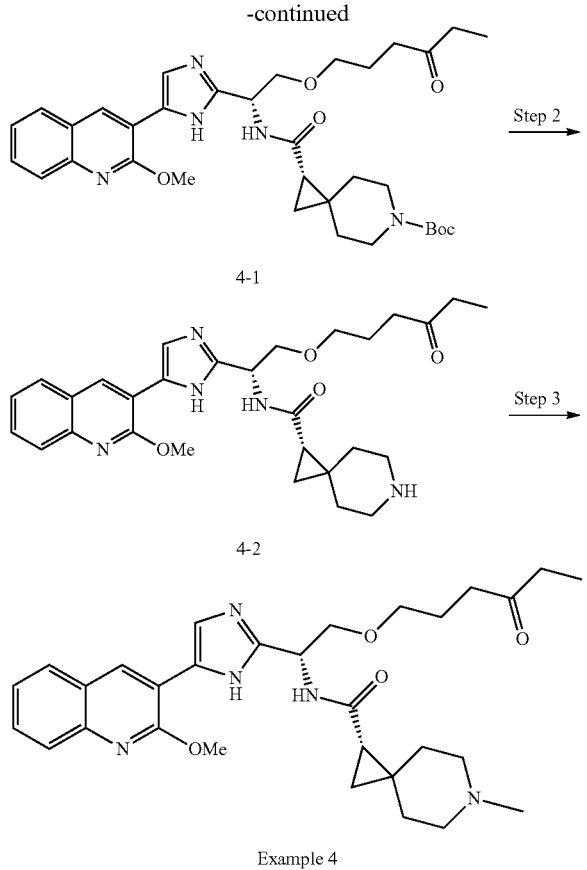

4-1

4-2

Example 4

Step 1: tert-butyl (S)-1-(((R)-1-(5-(2-methoxyquinolin-3-yl)-1H-imidazol-2-yl)-2-((4-oxohexyl)oxy)ethyl)carbamoyl)-6-azaspiro[2.5]octane-6-carboxylate (4-1)

To a solution of (R)-6-(2-amino-2-(5-(2-methoxyquinolin-3-yl)-1H-imidazol-2-yl)ethoxy)hexan-3-one (INTERMEDIATE A) (50 mg, 0.131 mmol) in DMF (654 μl) at ambient temperature was added (S)-6-(tert-butoxycarbonyl)-6-azaspiro[2.5]octane-1-carboxylic acid (B-4) (36.7 mg, 0.144 mmol), HATU (54.7 mg, 0.144 mmol), and DIPEA (45.7 μl 0.261 mmol). The mixture was stirred for 2 hours before acidifying with a few drops of AcOH. The mixture was purified by mass triggered reverse phase HPLC (MeCN/water with 0.1% TFA modifier) to afford the title compound. MS: 620.5 (M+1).

Step 2: (S)—N—((R)-1-(5-(2-methoxyquinolin-3-yl)-1H-imidazol-2-yl)-2-((4-oxohexyl)oxy)ethyl)-6-azaspiro[2.5]octane-1-carboxamide (4-2)

To a solution of (S)-tert-butyl 1-(((R)-1-(5-(2-methoxyquinolin-3-yl)-1H-imidazol-2-yl)-2-((4-oxohexyl)oxy)ethyl)carbamoyl)-6-azaspiro[2.5]octane-6-carboxylate (2-1) (50 mg, 0.081 mmol) in DCM (403 μl) at ambient temperature was added TFA (31.1 μl, 0.403 mmol). The mixture was stirred for 1 hour before concentrating and placing under vacuum to afford the title compound. MS: 520.4 (M+1).

Step 3: (S)—N—((R)-1-(5-(2-methoxyquinolin-3-yl)-1H-imidazol-2-yl)-2-((4-oxohexyl)oxy)ethyl)-6-methyl-6-azaspiro[2.5]octane-1-carboxamide (Example 4)

To a solution of (S)—N—((R)-1-(5-(2-methoxyquinolin-3-yl)-1H-imidazol-2-yl)-2-((4-oxohexyl)oxy)ethyl)-6-azaspiro[2.5]octane-1-carboxamide (20 mg, 0.038 mmol) in methanol (192 μl)/THF (192 μl) at ambient temperature was added formaldehyde (17.19 μl, 0.231 mmol) and sodium triacetoxyborohydride (24.47 mg, 0.115 mmol). The mixture was stirred for 2 hours before acidifying with a few drops of AcOH and concentrating. The mixture was purified by mass triggered reverse phase HPLC (MeCN/water with 0.1% TFA modifier) to afford the title compound. MS: 534.5 (M+1). NMR: (500 MHz, DMSO-d6) 9.33 (bs, 1H), 9.03 (m, 1H), 8.77 (d, J=26.9 Hz, 1H), 7.89 (dd, J=27.3, 7.7 Hz, 2H), 7.81 (d, J=8.4 Hz, 1H), 7.70 (t, J=7.5 Hz, 1H), 7.49 (t, J=7.3 Hz, 1H), 5.35-5.16 (m, 1H), 4.13 (s, 3H), 3.80 (dd, J=16.3, 6.0 Hz, 2H), 3.50-3.36 (m, 2H), 3.28-2.79 (m, 4H), 2.38-2.19 (m, 4H), 2.07 (t, J=12.2 Hz, 1H), 1.89-1.59 (m, 6H), 1.21 (dt, J=24.2, 7.0 Hz, 2H), 1.04 (t, J=4.7 Hz, 1H), 0.95 (dt, J=14.7, 7.5 Hz, 2H), 0.80 (t, J=7.3 Hz, 3H).

The following examples were prepared in an analogous manner to the procedures described above using appropriate starting materials described previously or that are commercially available.

| | Structure | Name | Exact Mass [M + H]+ | Observed [M + H]+ |
|---|---|---|---|---|
| 5 | 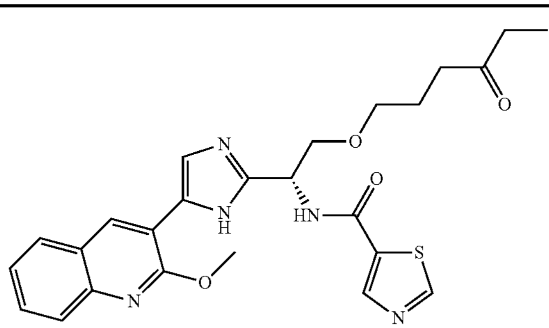 | N-{(1R)-1-[5-(2-methoxyquinolin-3-yl)-1H-imidazol-2-yl]-2-[(4-oxohexyl)oxy]ethyl}-1,3-thiazole-5-carboxamide | Calc'd 494.2, found | 494.2 |

-continued

| | Structure | Name | Exact Mass [M + H]+ | Observed [M + H]+ |
|---|---|---|---|---|
| 6 | 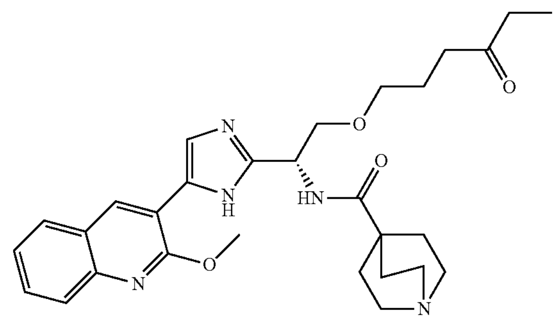 [SMILES: CCC(=O)CCCOC[C@H](NC(=O)C12CCN(CC1)CC2)c1ncc(-c2cc3ccccc3nc2OC)[nH]1] | N-{(1R)-1-[5-(2-methoxyquinolin-3-yl)-1H-imidazol-2-yl]-2-[(4-oxohexyl)oxy]ethyl}-1-azabicyclo[2.2.2]octane-4-carboxamide | Calc'd 520.3, found | 520.3 |
| 7 | 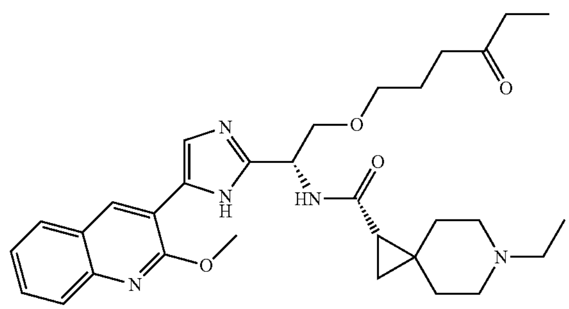 | (1S)-6-ethyl-N-{(1R)-1-[5-(2-methoxyquinolin-3-yl)-1H-imidazol-2-yl]-2-[(4-oxohexyl)oxy]ethyl}-6-azaspiro[2.5]octane-1-carboxamide | Calc'd 548.3, found | 548.4 |
| 8 | 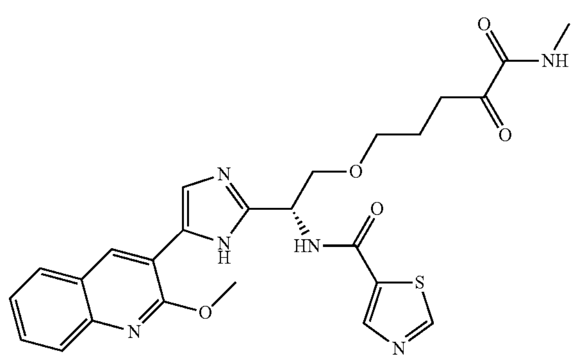 [SMILES: CNC(=O)C(=O)CCCOC[C@H](NC(=O)c1cncs1)c1ncc(-c2cc3ccccc3nc2OC)[nH]1] | N-[(1R)-1-[5-(2-methoxyquinolin-3-yl)-1H-imidazol-2-yl]-2-{[5-(methylamino)-4,5-dioxopentyl]oxy}ethyl]-1,3-thiazole-5-carboxamide | Calc'd 523.2, found | 523.2 |
| 9 | 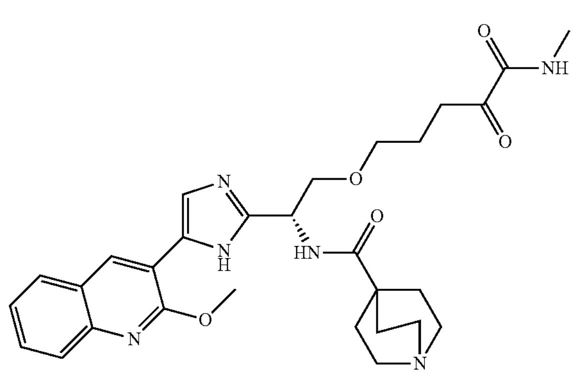 [SMILES: CNC(=O)C(=O)CCCOC[C@H](NC(=O)C12CCN(CC1)CC2)c1ncc(-c2cc3ccccc3nc2OC)[nH]1] | N-[(1R)-1-[5-(2-methoxyquinolin-3-yl)-1H-imidazol-2-yl]-2-{[5-(methylamino)-4,5-dioxopentyl]oxy}ethyl]-1-azabicyclo[2.2.2]octane-4-carboxamide | Calc'd 549.3, found | 549.3 |

| | Structure | Name | Exact Mass [M + H]+ | Observed [M + H]+ |
|---|---|---|---|---|
| 10 | 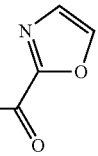 | N-{(1R)-1-[5-(2-methoxyquinolin-3-yl)-1H-imidazol-2-yl]-2-[4-(1,3-oxazol-2-yl)-4-oxobutoxy]ethyl}-1,3-thiazole-5-carboxamide | Calc'd 533.2, found | 533.2 |
| 11 | 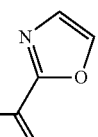 | (1S)-N-{(1R)-1-[5-(2-methoxyquinolin-3-yl)-1H-imidazol-2-yl]-2-[4-(1,3-oxazol-2-yl)-4-oxobutoxy]ethyl}-6-methyl-6-azaspiro[2.5]octane-1-carboxamide | Calc'd 573.3, found | 573.3 |
| 12 | 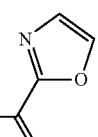 | N-{(1R)-1-[5-(2-methoxyquinolin-3-yl)-1H-imidazol-2-yl]-2-[4-(1,3-oxazol-2-yl)-4-oxobutoxy]ethyl}-1-azabicyclo[2.2.2]octane-4-carboxamide | Calc'd 559.3, found | 559.3 |
| 13 | 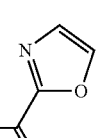 | N-{(1R)-1-[5-(2-methoxyquinolin-3-yl)-1H-imidazol-2-yl]-2-[4-(1,3-oxazol-2-yl)-4-oxobutoxy]ethyl}-N~2~,N~2~-dimethylglycinamide | Calc'd 507.2, found | 507.4 |

-continued

| | Structure | Name | Exact Mass [M + H]+ | Observed [M + H]+ |
|---|---|---|---|---|
| 14 | 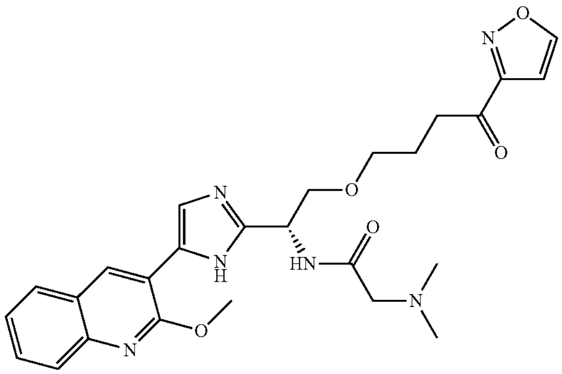 [SMILES: COc1nc2ccccc2cc1-c1cnc([C@H](COCCCC(=O)c2ccon2)NC(=O)CN(C)C)[nH]1] | N-{(1R)-2-(4-isoxazol-3-yl-4-oxobutoxy)-1-[5-(2-methoxyquinolin-3-yl)-1H-imidazol-2-yl]ethyl}-N~2~,N~2~-dimethylglycinamide | Calc'd 507.2, found | 507.2 |
| 15 | 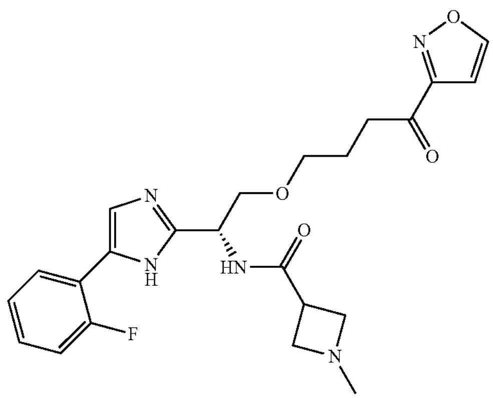 [SMILES: CN1CC(C(=O)N[C@@H](COCCCC(=O)c2ccon2)c2ncc(-c3ccccc3F)[nH]2)C1] | N-[(1R)-1-[5-(2-fluorophenyl)-1H-imidazol-2-yl]-2-(4-isoxazol-3-yl-4-oxobutoxy)ethyl]-1-methylazetidine-3-carboxamide | Calc'd 456.2, found | 456.4 |
| 16 | 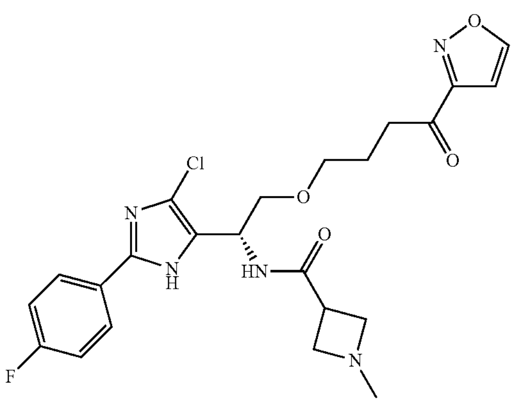 [SMILES: CN1CC(C(=O)N[C@@H](COCCCC(=O)c2ccon2)c2[nH]c(-c3ccc(F)cc3)nc2Cl)C1] | N-[(1R)-1-[4-chloro-2-(4-fluorophenyl)-1H-imidazol-5-yl]-2-(4-isoxazol-3-yl-4-oxobutoxy)ethyl]-1-methylazetidine-3-carboxamide | Calc'd 490.2, found | 490.3 |
| 17 | 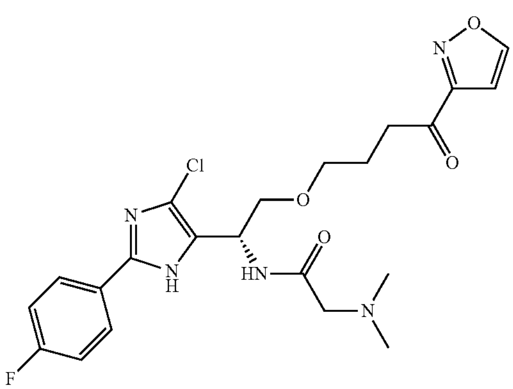 [SMILES: CN(C)CC(=O)N[C@@H](COCCCC(=O)c1ccon1)c1[nH]c(-c2ccc(F)cc2)nc1Cl] | N-[(1R)-1-[4-chloro-2-(4-fluorophenyl)-1H-imidazol-5-yl]-2-(4-isoxazol-3-yl-4-oxobutoxy)ethyl]-N~2~,N~2~-dimethylglycinamide | Calc'd 478.2, found | 478.3 |

-continued

| | Structure | Name | Exact Mass [M + H]+ | Observed [M + H]+ |
|---|---|---|---|---|
| 18 | 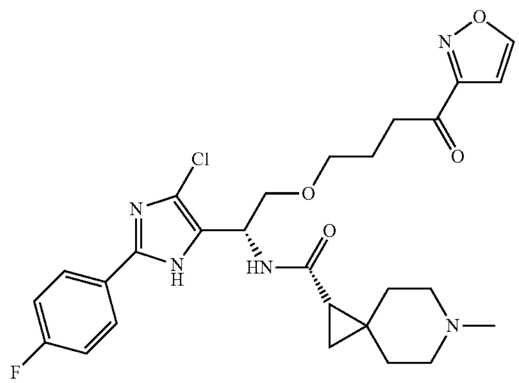 | (1S)-N-[(1R)-1-[4-chloro-2-(4-fluorophenyl)-1H-imidazol-5-yl]-2-(4-isoxazol-3-yl-4-oxobutoxy)ethyl]-6-methyl-6-azaspiro[2.5]octane-1-carboxamide | Calc'd 544.2, found | 544.4 |
| 19 | 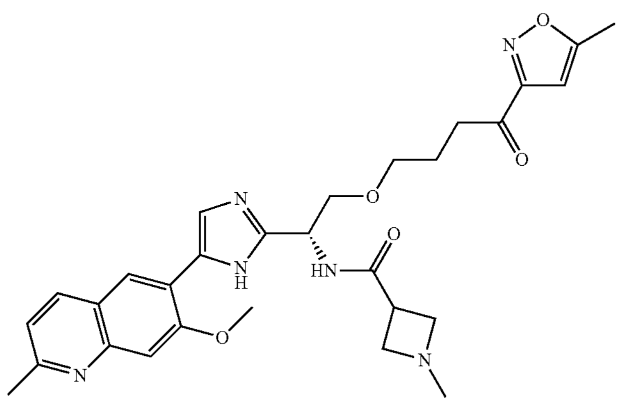 | N-{(1R)-1-[5-(7-methoxy-2-methylquinolin-6-yl)-1H-imidazol-2-yl]-2-[4-(5-methylisoxazol-3-yl)-4-oxobutoxy]ethyl}-1-methylazetidine-3-carboxamide | Calc'd 547.3, found | 547.5 |
| 20 | 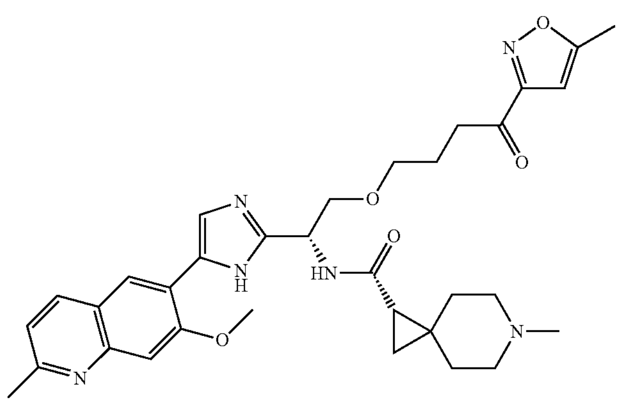 | (1S)-N-{(1R)-1-[5-(7-methoxy-2-methylquinolin-6-yl)-1H-imidazol-2-yl]-2-[4-(5-methylisoxazol-3-yl)-4-oxobutoxy]ethyl}-6-methyl-6-azaspiro[2.5]octane-1-carboxamide | Calc'd 601.3, found | 601.6 |
| 21 | 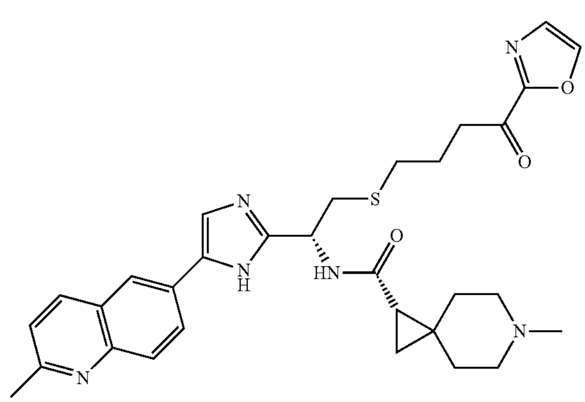 | (1S)-6-methyl-N-[(1R)-1-[5-(2-methylquinolin-6-yl)-1H-imidazol-2-yl]-2-{[4-(1,3-oxazol-2-yl)-4-oxobutyl]sulfanyl}ethyl]-6-azaspiro[2.5]octane-1-carboxamide | Calc'd 573.3, found | 573.1 |

Human HDAC Enzyme Inhibitor Fluor-De-Lys Assay
Materials

Recombinant human HDAC8 (catalog number BML-SE145-0100) and HDAC10 (catalog number BML-SE559-0050) enzymes, HDAC substrates BML-KI104 and BML-KI178, and HDAC developer solutions BML-KI105 and BML-KI176 were purchased from Enzo Life Sciences (Farmingdale, NY). Recombinant human HDAC5 and HDAC11 were purchased from BPS Bioscience (San Diego, CA)(catalog numbers 50045 and 50021). Substrate Boc-Lys (TFA)-AMC was obtained from Bachem (Bupendorf, Switzerland) (catalog number 1-1985). HDAC inhibitor suberoylanilide hydroxamic acid (SAHA) was obtained from Indofine (Hillsborough Township, NJ) and trichostatin A (TSA) was obtained from Sigma-Aldrich (St. Louis, MO). D-myo inositol-1,4,5,6-tetraphosphate potassium salt ($IP_4$) was obtained from Carbosynth (San Diego, CA) (catalog MI 16761). HEPES pH 8.0 was obtained from Boston BioProducts (Ashland, MA), Tween-20 from Fisher Scientific (Hampton, NH)(catalog number BP337), TCEP from Calbiochem and 7.5% bovine serum albumin (BSA) from Life Technologies (Carlsbad, CA) (catalog number 15260037). 384-well, black assay plates were obtained from Corning (Corning, NY) (catalog number 3575).

Recombinant human HDAC1, HDAC2, and HDAC3/SMRT heterodimer were prepared by Merck Research Laboratories. Full length human HDAC1-FLAG was stably expressed in HEK-293F cells and purified using an anti-FLAG affinity chromatography with FLAG peptide (100 μg/ml) elution. The final concentration of HDAC1 was 1.98 uM by Western Blot analysis and 1.39 uM by active site titration. Full length human HDAC2-FLAG was expressed in baculovirus infected Sf9 cells and purified using an anti-FLAG affinity chromatography with FLAG peptide (100 μg/ml) elution. The eluted protein was then passed over an anti-HDAC1 immunoaffinity column to remove any complexes containing HDAC1. The final concentration of HDAC2 was 16.8 uM by Western Blot analysis and 7.6 uM by active site titration. Full length human HDAC3-FLAG was expressed in HEK-293F cells along with SMRT (amino acids 1-899)-6×His; plasmid APP-0024) and purified using an anti-FLAG affinity chromatography with FLAG peptide (100 μg/ml) elution. The eluted protein was then passed over an anti-HDAC1 immunoaffinity column to remove any complexes containing HDAC1. The final concentration of the HDAC3/SMRT complex was 2.03 uM by Western Blot analysis and 1.37 uM by active site titration.

HDAC Inhibition Assays

The histone deacetylase activities of HDAC1, HDAC2, HDAC3, HDAC6, and HDAC8 were measured in modified Fluor-de-Lys assays in 384-well format. In this assay, HDAC enzymes are initially incubated with an ε-acetyl (or -trifluoroacetyl)-L-lysine-containing substrate with a C-terminal amide having aminomethylcoumarin as the amine component. HDACs cleave the ε-acetyl group, rendering the resulting product susceptible to AMC cleavage by trypsin. The released AMC is then detected by its fluorescence.

The HDAC 1, 2 assays employed buffer A, which contained 20 mM HEPES, pH 8.0, 1 mM $MgCl_2$, 137 mM NaCl, 2.7 mM KCl, 0.05% BSA. The HDAC3/SMRT assay employed buffer B, consisting of 20 mM HEPES, pH 8.0, 1 mM $MgCl_2$, 50 mM NaCl, 2.7 mM KCl, 0.05% BSA, 0.005% Tween 20, and 10 μM $IP_4$. The HDAC6 assay employed buffer C, consisting of 20 mM HEPES, pH 8.0, 1 mM $MgCl_2$, 137 mM NaCl, 2.7 mM KCl, 0.5 mM TCEP (Calbiochem) and 0.05% BSA. The HDAC8 assay employed buffer D, consisting of 20 mM HEPES, pH 8.0, 1 mM $MgCl_2$, 100 mM NaCl, 20 mM KCl, 0.1% n-octyl-β-D-glucoside (Anatrace, Maumee, OH) and 0.05% BSA. All steps were performed at room temperature (23° C.). The assay was performed by pre-incubating serial dilutions of test compounds with the target HDAC prior to initiation with substrate. Each compound was titrated in a 10-point dose response, using a 1:3 fold dilution scheme, with 0.15 ul of solution added by ECHO555 to the plate, followed by the addition of 20 μl of the appropriate HDAC isoform diluted in appropriate assay buffer. The incubation was allowed to proceed for 3 hours, then the appropriate substrate diluted in assay buffer (final substrate concentration ~$K_m$) was added and the reaction allowed to proceed for 60 min. Final conditions used for each assay were: 1. HDAC 1, 0.3 nM total enzyme, 20 μM substrate BML-K1104; 2. HDAC 2, 1.5 nM total enzyme, 40 μM substrate BML-K1104; 3. HDAC 3/SMRT, 0.3 nM total enzyme, 20 μM substrate BML-K1104; 4. HDAC 6, 1.3 nM total enzyme, 2.5 μM substrate BML-K1104; 5. HDAC 8, 1.3 nM total enzyme, 200 μM substrate BML-K1178; the final high dose of test compound was 30 μM. For potent compounds, 900 nM was used as the final high dose. The reactions were stopped and developed by addition of 30 ul of HDAC developer solution containing a saturating level of HDAC inhibitor as follows: 1. HDACs 1, 2, 3 and 6, developer BML-KI105 (stock diluted 1:125, containing 20 uM SAHA, 2. HDAC 8, developer BML-KI176 (1:100 plus 40 uM SAHA, and the plates were shaken to assure good mixing, briefly centrifuged, incubated for 30 minutes at room temperature and then the fluorescence intensity (excitation 380 nm, emission 460 nm) measured using a PHERAstar plate reader. For each assay plate, both minimal inhibition (100% DMSO; 0% inhibition) and maximal inhibition (either 10 uM SAHA or 100 uM TSA; 100% inhibition) controls were added. For data analysis, background subtracted product (fluorescence) vs. time data for each inhibitor concentration was fitted using a 4-parameter fit.

All compounds prepared were tested in the binding assays with HDAC1, 2, 3, 6 and 8.

KARN Assay
Cell Maintenance

KARN cells (Jurkat 2C4) were licensed from the laboratory of Dr. John Karn, Case Western Reserve University, School of Medicine. The details regarding this cell line are published (Pearson, R., Kin, Y. K., Hokello, J., Lassen, K., Friedman, J., Tyagi, M., Karn, J., 2008, *J. Virol.* 82:12291-12303). The cells were grown in a T175 flask (Thermo Fisher, catalog number 159910) in RPMI 1640 containing L-glutamine and phenol red (Life Technologies, catalog number 11875-085), 5% heat inactivated fetal bovine serum (FBS; Life Technologies, catalog number 10100-147) and 100 μg/ml Penicillin-Streptomycin (Life Technologies, catalog number 15140-122) at 37° C. An atmosphere of 5% $CO_2$ and 90% humidity was used for all culture work. Cells were split and reseeded into T175 flasks at a density of $0.2 \times 10^6$ cells/ml, in 40 ml of media, every 3-4 days.

KARN Assay

Day 1: After the 3-4 day growth period, the cells were transferred from the T175 flask to a 50 ml conical tube and gently pelleted at 1000 rpm for 5 minutes. The supernatant was removed and the cells gently resuspended in assay media RPMI 1640 medium containing L-glutamine but without Phenol Red (Life Technologies, catalog number 11835-030), 5% FBS and 100 μg/ml Penicillin-Streptomycin, and then reseeded such that the original flask is now divided into two T175 flasks. These flasks were returned to the incubator.

Day 2: Cell Preparation: The next day, the cells were transferred from each T175 flask to an individual 50 ml conical tube and gently pelleted at 1000 rpm for 5 minutes. The cells were gently resuspended in assay media (30 ml) and pelleted again. The cell pellets were each resuspended in 30 ml of RPMI 1640 medium containing L-glutamine but without Phenol Red, 100 µg/ml Penicillin-Streptomycin and containing either 0.1% or 5% normal human serum (NHS; Biospecialty, Colmar, PA, catalog number 115-00 Anticoagulant free). The cells were counted using the ViCell (Beckman Coulter, Brea, CA) and diluted as necessary. A Multidrop (Combi, Thermo Scientific, Waltham, MA) with a sterile head was used to seed the cells into the wells of a 384-well solid black plate with lid (Perkin Elmer, Waltham, MA, catalog number 6007660) at 4000 cells/30 µl/well for the 5% NHS assay media and 6000 cells/30 µl/well for 0.1% NHS assay. The plates were covered and returned to the incubator prior to compound addition.

Compound Preparation: Solutions of control inhibitor suberoylanilide hydroxamic acid (SAHA; Sigma, catalog number SML0061) and test compounds in 100% DMSO were titrated into 384-well polypropylene plates (Labcyte, San Jose, CA, catalog number P-05525) using a 20-point dose response and 2-fold dilutions. The reference compounds, DMSO and SAHA were then added to the compound plate. Using the Access system (Labcyte), 120 nl of these inhibitor and control solutions were added to the individual wells of the plates containing the cells, and the plates were then returned to the incubator for ~20 hr (range from 18-24 hr). The final high concentration for SAHA and the test compounds in the assays was 40 µM. The final DMSO concentration in all wells was 0.4%. The minimal induction reference compound used was DMSO and the maximal induction reference compound used was SAHA (2 µM final concentration in the assay).

Day 3: The luciferase detection reagent was prepared by transferring the contents of one bottle of Steady-Glo buffer to one bottle of Steady-Glo substrate (Steady-Glo Luciferase Assay System, Promega, Madison, MI, catalog number E2520), followed by gently mixing until the substrate was thoroughly dissolved and the solution was equilibrated to room temperature. The cell culture assay plates were removed from the incubator and brought to room temperature (15 min). The Steady-Glo Reagent was added to the plates (30 µl/well), which were then covered with a black lid and incubated for 10 minutes at room temperature. The plates were then read for luminescence on an Envision (Perkin Elmer) using the ultrasensitive mode (US LUM), 0.1 counts per second and 384-well aperture. Luminescence counts in the DMSO reference wells were considered as 0% induction, while those in the 2 µM SAHA reference wells were considered as 100% induction. Dose response curves were plotted as test compound concentration (X-axis) vs. percent activation (Y-axis) using a 4-parameter fit based on the Levenberg-Marquardt algorithm.

The HDAC and Karn potency data of compounds 1-21 are as follows:

| ID | HDAC1_IC$_{50}$ (nM) | HDAC2_IC$_{50}$ (nM) | HDAC3_IC$_{50}$ (nM) | HDAC6_IC$_{50}$ (nM) | HDAC8_IC$_{50}$ (nM) | Karn 0.1% NHS (nM) | Karn 5% NHS (nM) |
|---|---|---|---|---|---|---|---|
| 1 | 287.6 | 1002 | 185.2 | — | — | 11710 | — |
| 2 | 601.9 | 900 | 271.9 | >900 | >900 | 18480 | 23900 |
| 3 | 671.2 | 4348 | 297.9 | — | — | — | — |
| 4 | 89.8 | 339.6 | 46.4 | 23320 | >45000 | — | — |
| 5 | 312.9 | 1161 | 63.4 | >45000 | 2721 | — | — |
| 6 | 258.2 | 925.4 | 87.3 | >45000 | >45000 | 8969 | 14490 |
| 7 | 52.5 | 278 | 32.4 | 19040 | >45000 | 2351 | 3497 |
| 8 | 1.5 | 2.5 | 1.5 | 5107 | 3857 | 80.2 | 408.3 |
| 9 | 1.5 | 1.5 | 1.5 | >45000 | 3375 | 232.5 | 465.7 |
| 10 | 6.6 | 25.9 | 3.6 | >45000 | 1381 | 295.3 | 1501 |
| 11 | 2.1 | 9.7 | 5.0 | >45000 | 7780 | 59.8 | 218.4 |
| 12 | 4.7 | 29.7 | 7.7 | >45000 | 5551 | 252.2 | 562 |
| 13 | 2.7 | 14.4 | 3.8 | >45000 | 16980 | 424.2 | 854 |
| 14 | 1.5 | 3.2 | 2.2 | >45000 | 1755 | 83.8 | 252.1 |
| 15 | 4.0 | 31.3 | 1.6 | >900 | >900 | 538.7 | 548.2 |
| 16 | 11.8 | 56.7 | 9.2 | >900 | >900 | 979.4 | 1104 |
| 17 | 18.6 | 106.4 | 17.0 | >900 | >900 | 1486 | 2423 |
| 18 | 1.4 | 8.1 | 1.3 | >900 | >900 | 77.7 | 109.2 |
| 19 | 6.9 | 8.0 | 1.3 | 468.6 | >900 | 374.1 | 448.8 |
| 20 | 3.7 | 3.8 | 0.8 | >900 | >900 | 40.5 | 55.1 |
| 21 | 1.5 | 2.9 | 1.5 | 19310 | 1052 | 60.7 | 64.4 |

Treatment or Prevention of HIV Infection

The Compounds of Formula I may be useful in the activation of HIV latency, the the treatment of HIV infection and/or reduction of the likelihood or severity of symptoms of HIV infection and the inhibition of HIV viral replication and/or HIV viral production in a cell-based system. For example, the Compounds of Formula I may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Compound of Formula I or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Compounds of Formula I are also useful in the preparation and execution of screening assays for antiviral compounds. For example the Compounds of Formula I may be useful for identifying resistant HIV cell lines harboring mutations, which are excellent screening tools for more powerful antiviral compounds. Furthermore, the Compounds of Formula I may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Compounds of Formula I.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: I at least one Compound of Formula I (which may include two or more different Compounds of Formula I), or a pharmaceutically acceptable salt or prodrug thereof, and (ii) at least one additional therapeutic agent that is other than a Compound of Formula I, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Compound of Formula I is administered during a time when the additional therapeutic agent(s) exert their prophylactic or therapeutic effect, or vice versa.

In another embodiment, at least one Compound of Formula I and the additional therapeutic agent(s) are administered in doses commonly employed when such agents are used as monotherapy for treating a viral infection.

In another embodiment, at least one Compound of Formula I and the additional therapeutic agent(s) are administered in doses lower than the doses commonly employed when such agents are used as monotherapy for treating a viral infection.

In still another embodiment, at least one Compound of Formula I and the additional therapeutic agent(s) act synergistically and are administered in doses lower than the doses commonly employed when such agents are used as monotherapy for treating a viral infection.

In one embodiment, at least one Compound of Formula I and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Compound of Formula I and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Compound of Formula I and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
| --- | --- |
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | Pifeltro ® |
| doravirine + lamivudine + tenofovir DF | Delstrigo ® |
| efavirenz, EFV | Sustiva ®, Stocrin ® |
| efavirenz + emtricitabine + tenofovir DF | Atripla ® |
| EFdA (4'-ethynyl-2-fluoro-2'-deoxyadenosine) | |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |
| raltegravir | Isentress ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |

TABLE A-continued

| Name | Trade Name |
|---|---|
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In one embodiment, one or more anti-HIV drugs are selected from, raltegravir, lamivudine, abacavir, ritonavir, darunavir, atazanavir, emtricitabine, tenofovir, rilpivirine, doravirine, EFdA and lopinavir.

In another embodiment, the compound of formula I is used in combination with raltegravir.

In another embodiment, the compound of formula I is used in combination with lamivudine.

In still another embodiment, the compound of formula I is used in combination atazanavir.

In another embodiment, the compound of formula I is used in combination with darunavir.

In another embodiment, the compound of formula I is used in combination with rilpivirine.

In one embodiment, the compound of formula I is used in combination with lamivudine and abacavir.

In another embodiment, the compound of formula I is used in combination with EFdA.

In another embodiment, the compound of formula I is used in combination with emtricitabine and tenofovir.

In still another embodiment, the compound of formula I is used in combination doravirine.

In another embodiment, the compound of formula I is used in combination with ritonavir and lopinavir.

In one embodiment, the compound of formula I is used in combination with abacavir and lamivudine.

In another embodiment, the compound of formula I is used in combination with lopinavir and ritonavir.

In one embodiment, the present invention provides pharmaceutical compositions comprising (i) a compound of formula I or a pharmaceutically acceptable salt or prodrug thereof (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula I or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Compounds of Formula I may be administered as a component of a composition that comprises a pharmaceutically acceptable carrier or vehicle. The present invention provides pharmaceutical compositions comprising an effective amount of at least one Compound of Formula I and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I are administered orally.

In another embodiment, the one or more Compounds of Formula I are administered intravenously.

In one embodiment, a pharmaceutical preparation comprising at least one Compound of Formula I is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I by weight or volume. In various embodiments, the present compositions can contain, in one embodiment, from about 1% to about 70% or from about 5% to about 60% of the Compound(s) of Formula I by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I may be administered at varying frequencies. In one embodiment, a unit dosage of a Compound of Formula I may be administered once daily. In another embodiment, a unit dosage of a Compound of Formula I may be administered twice weekly. In another embodiment, a unit dosage of a Compound of Formula I may be administered once weekly. In still another embodiment, a unit dosage of a Compound of Formula I may be administered once biweekly. In another embodiment, a unit dosage of a Compound of Formula I may be administered once monthly. In yet another embodiment, a unit dosage of a Compound of Formula I may be administered once bimonthly. In another embodiment, a unit dosage of a Compound of Formula I may be administered once every 3 months. In a further embodiment, a unit dosage of a Compound of Formula I may be administered once every 6 months. In another embodiment, a unit dosage of a Compound of Formula I may be administered once yearly.

The amount and frequency of administration of the Compounds of Formula I will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Compound of Formula I, or a pharmaceutically acceptable salt or prodrug of said compound and a pharmaceutically acceptable carrier, vehicle or diluent.

In another aspect the present invention provides a kit comprising an amount of at least one Compound of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I and the one or more additional therapeutic agents are provided in the same container. In one embodiment, the one or more Compounds of Formula I and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound selected from:
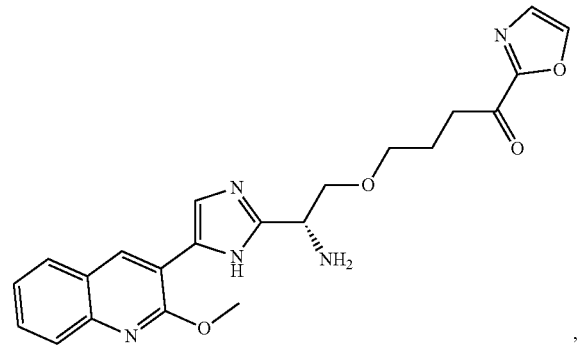
,
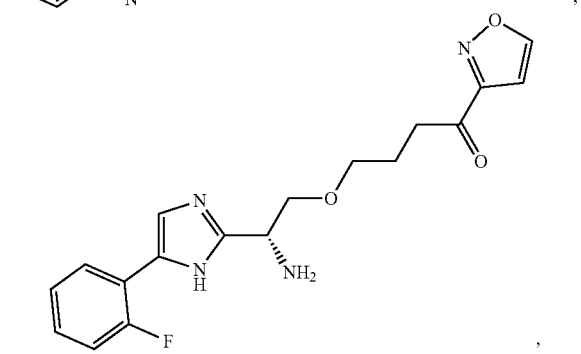
,
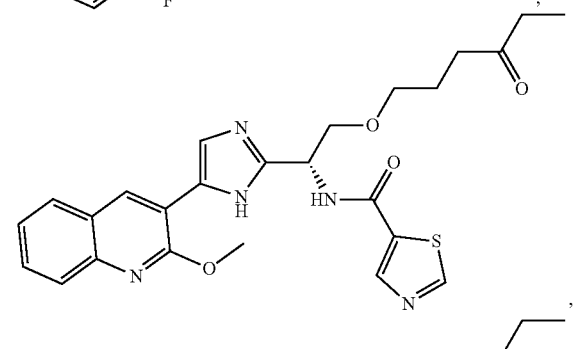
,
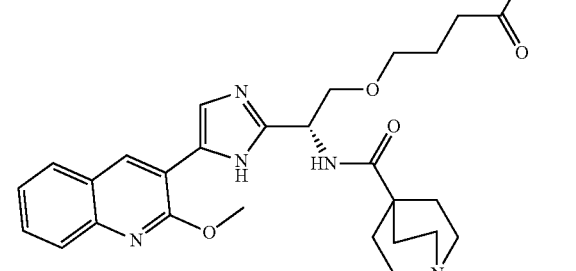
,
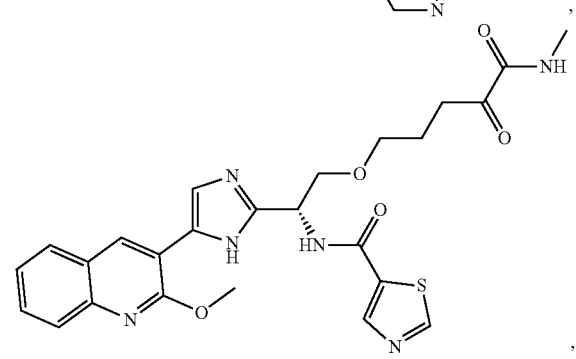
,
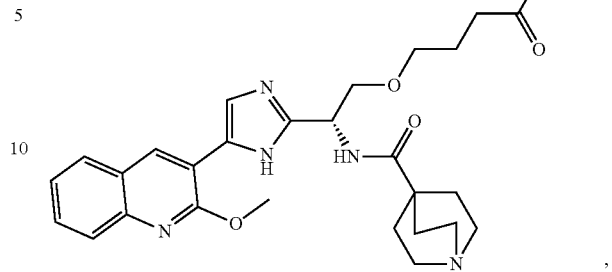
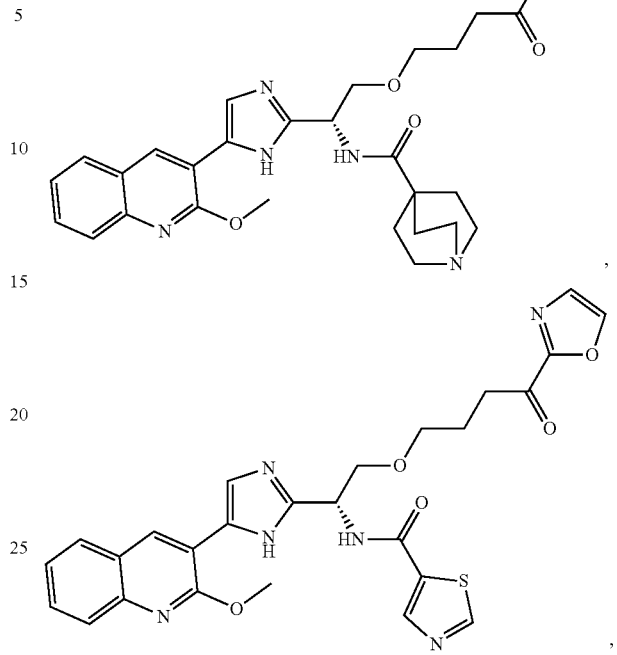
,
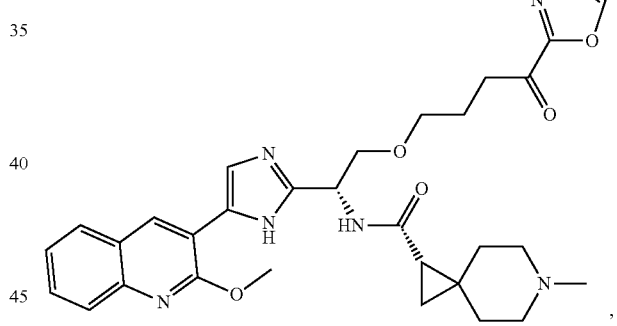
,
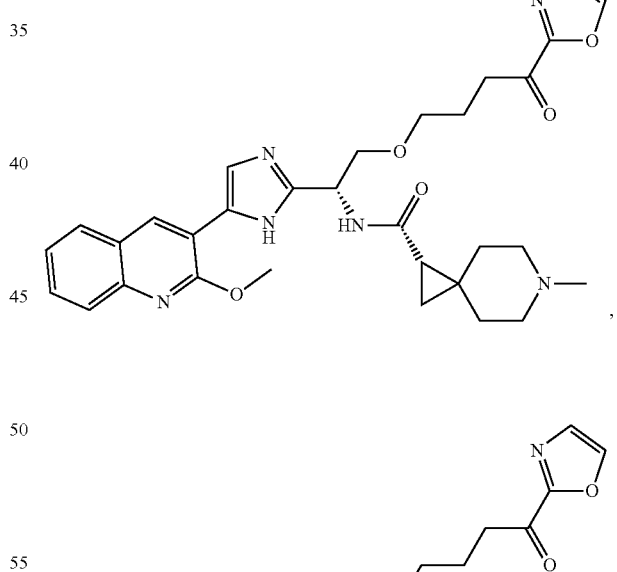
,
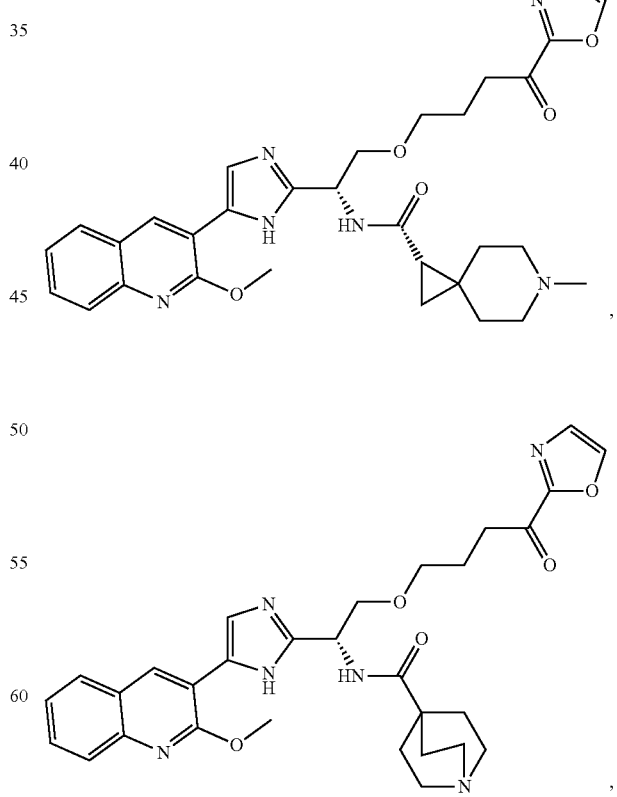
,

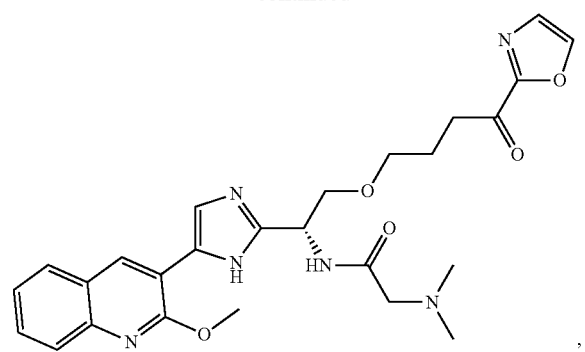
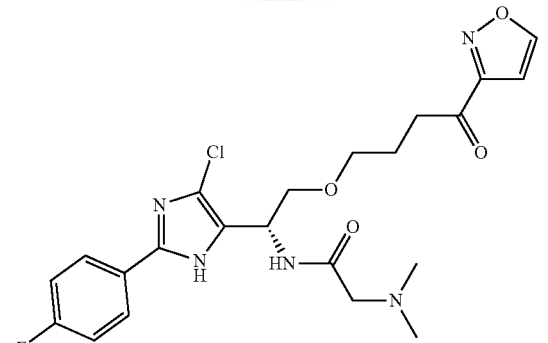
or a pharmaceutically acceptable salt thereof.

2. A pharmaceutical composition comprising an effective amount of a compound of claim 1, or a pharmaceutically acceptable salt thereof, and a pharmaceutically acceptable carrier.

3. A method for inhibiting histone deacetylase (HDAC) in a subject in need thereof which comprises administering to the subject an effective amount of a compound of claim 1, or a pharmaceutically acceptable salt thereof.

4. A method for treating an infection by HIV or for treating or delaying the onset or progression of AIDS in a subject in need thereof, which comprises administering to the subject an effective amount of compound of claim 1, or a pharmaceutically acceptable salt thereof.

5. The pharmaceutical composition of claim 2, further comprising one or more additional therapeutic agents selected from lamivudine, abacavir, ritonavir, darunavir, atazanavir, emtricitabine, tenofovir, rilpivirine, doravirine, EFdA and lopinavir.

6. The method of claim 4, further comprising administering to the subject one or more additional therapeutic agents selected from lamivudine, abacavir, ritonavir, darunavir, atazanavir, emtricitabine, tenofovir, rilpivirine, doravirine, EFdA and lopinavir, wherein the amounts administered are together effective to treat infection by HIV or to treat, prevent or delay the onset or progression of AIDS.

7. The pharmaceutical composition of claim 2, wherein the composition is present in a tablet or capsule.

8. The pharmaceutical composition of claim 2, wherein the composition is present in a liquid form preparation.

9. A pharmaceutically acceptable prodrug of the compound of claim 1.

* * * * *